US007572454B2

(12) United States Patent
Jackson et al.

(10) Patent No.: US 7,572,454 B2
(45) Date of Patent: Aug. 11, 2009

(54) T HELPER CELL EPITOPES

(75) Inventors: David Charles Jackson, Victoria (AU); Souravi Ghosh, Victoria (AU); John Walker, Victoria (AU)

(73) Assignees: CSL Limited, Victoria (AU); The University of Melbourne, Victoria (AU)

( * ) Notice: Subject to any disclaimer, the term of this patent is extended or adjusted under 35 U.S.C. 154(b) by 0 days.

(21) Appl. No.: 11/812,458

(22) Filed: Jun. 19, 2007

(65) Prior Publication Data
US 2007/0248615 A1 Oct. 25, 2007

Related U.S. Application Data

(60) Continuation of application No. 11/417,131, filed on May 4, 2006, now Pat. No. 7,241,448, which is a division of application No. 10/705,819, filed on Nov. 13, 2003, now Pat. No. 7,097,844, which is a division of application No. 09/890,650, filed as application No. PCT/AU00/00070 on Feb. 7, 2000, now Pat. No. 6,685,947.

(30) Foreign Application Priority Data

Feb. 5, 1999 (AU) .................................. PP8533
Aug. 4, 1999 (AU) .................................. PQ2013

(51) Int. Cl.
*A61K 39/175* (2006.01)

(52) U.S. Cl. .................................. 424/213.1; 530/300

(58) Field of Classification Search .............. 424/213.1, 424/186.1; 530/300
See application file for complete search history.

(56) References Cited

U.S. PATENT DOCUMENTS

| 5,756,102 A | 5/1998 | Paoletti et al. ........... 424/199.1 |
| 6,309,647 B1 | 10/2001 | Paoletti et al. ........... 424/199.1 |
| 7,097,844 B2 | 8/2006 | Jackson et al. .......... 424/213.1 |

OTHER PUBLICATIONS

Obeid, E.O., et al; "Protection against Morbillivirus-Induced Encephalitis by Immunization with a Rationally Designed Synthetic Peptide Vaccine Containing B- and T-Cell Epitopes from the Fusion Protein of Measles Virus"; *Journal of Virology*; vol. 69, No. 3; pp. 1420-1428, Mar. 1, 1995; XP 000608455.
Beauverger, P., et al; "Analysis of the Contribution of CTL Epitopes in the Immunobiology of Morbillivirus Infection"; *Virology*; vol. 219; pp. 133-139 (1996) XP 002268219.
Muenchbach, M. et al; "Quantitation and Facilitated De Novo Sequencing of Proteins by Isotopic N-Terminal Labeling of Peptides with a Fragmentation-Directing Moiety"; *Analytical Chemistry, American Chemical Society*, Columbus, US, vol. 72, No. 17, pp. 4047-4057; (2000), XP-001155607.

Barcley, P.L., et al; "Labelling of the Cytoplasmic Domains of Ovine Rhodopsin with Hydrophilic Chemical Probes"; *Biochemical Journal, Portland Press*, London, GB; vol. 220, No. 1, pp. 75-84 (1984), XP-009024239.
Glocker, M.O., et al; "Molecular Characterization of Surface Topology in Protein Tertiary Structures by Amino-Acylation and Mass Spectrometric Peptide Mapping"; *Bioconjugate Chemistry, American Chemical Society*, Washington, DC; vol. 5, No. 6, pp. 583-590 (1994) XP-001154401.
Gygi, S.P., et al; "Quantitative Analysis of Complex Protein Mixtures Using Isotope-coded Affinity Tags"; *Nature Biotechnology, Nature Publishing*, US; vol. 17, No. 10, pp. 994-999 (Oct. 1999), XP-001010578.
James, Peter; "Protein Expression Analysis: From 'Tip of the Iceberg' to a Global Method"; *Disease Markers, Wiley Chchester*, GB; vol. 17, No. 4, pp. 235-246 (2001) XP-002226421.
Partidos, Charalamobos, D., et al; "Prediction and Identification of a T Cell Epitope in the Fusion Protein of Measles Virus Immunodominant in Mice and Humans"; *Journal of General Virology*; vol. 71, pp. 2099-2105 (1990).
Visser at al, "Fusion protein nucleotide sequence similarities . . . ," *Journal of General Virology*, vol. 74, pp. 1989-1994 (1993).
Curran et al, "The fusion protein gene of phocine distemper virus: nucleotide . . . ," *Arch Virol*, vol. 126, pp. 159-169 (1992).
Kovamees et al, "The nucleotide sequence and deduced amino acid composition of the . . . ," *Journal of General Virology*, vol. 72, pp. 2959-2966 (1991).

(Continued)

*Primary Examiner*—Ali R. Salimi
(74) *Attorney, Agent, or Firm*—Nixon & Vanderhye

(57) ABSTRACT

The present invention provides T helper cell epitopes and compositions for use in inducing an immune response comprising at least one of these epitopes. The epitopes are contained within a peptide sequence selected from the group consisting of SSKTQTHTQQDRPPQPS (SEQ ID NO: 1); QPSTELEETRTSRARHS (SEQ ID NO: 2); RHSTTSAQRSTHYDPRT (SEQ ID NO: 3); PRTSDRPVSYTMNRTRS (SEQ ID NO: 4); TRSRKQTSHRLKNIPVH (SEQ ID NO: 5); SHQYLVIKLIPNASLIE (SEQ ID NO: 6); IGTDNVHYKIMTRPSHQ (SEQ ID NO: 7); YKIMTRPSHQYLVIKLI (SEQ ID NO: 8); KLIPNASLIENCTKAEL (SEQ ID NO: 9); AELGEYEKLLNSVLEPI (SEQ ID NO: 10); KLLNSVLEPINQALTLM (SEQ ID NO: 11); EPINQALTLMTKNVKPL (SEQ ID NO: 12); FAGVVLAGVALGVATAA (SEQ ID NO: 13); GVALGVATAAQITAGIA (SEQ ID NO: 14); TAAQITAGIALHQSNLN (SEQ ID NO: 15); GIALHQSNLNAQAIQSL (SEQ ID NO: 16); NLNAQAIQSLRTSLEQS (SEQ ID NO: 17); QSLRTSLEQSNKAIEEI (SEQ ID NO: 18); EQSNKAIEEIRETQET (SEQ ID NO: 19); TELLSIFGPSLRDPISA (SEQ ID NO: 20); PRYIATNGYLISNFDES (SEQ ID NO: 21); CIRGDTSSCARTLVSGT (SEQ ID NO: 22); DESSCVFVSESAICSQN (SEQ ID NO: 23); TSTIINQSPDKLLTFIA (SEQ ID NO: 24), SPDKLLTFIASDTCPLV (SEQ ID NO: 25) and SGRRQRRFAGVVLAGVA (SEQ ID NO: 26).

16 Claims, 13 Drawing Sheets

OTHER PUBLICATIONS

Figure 2A:
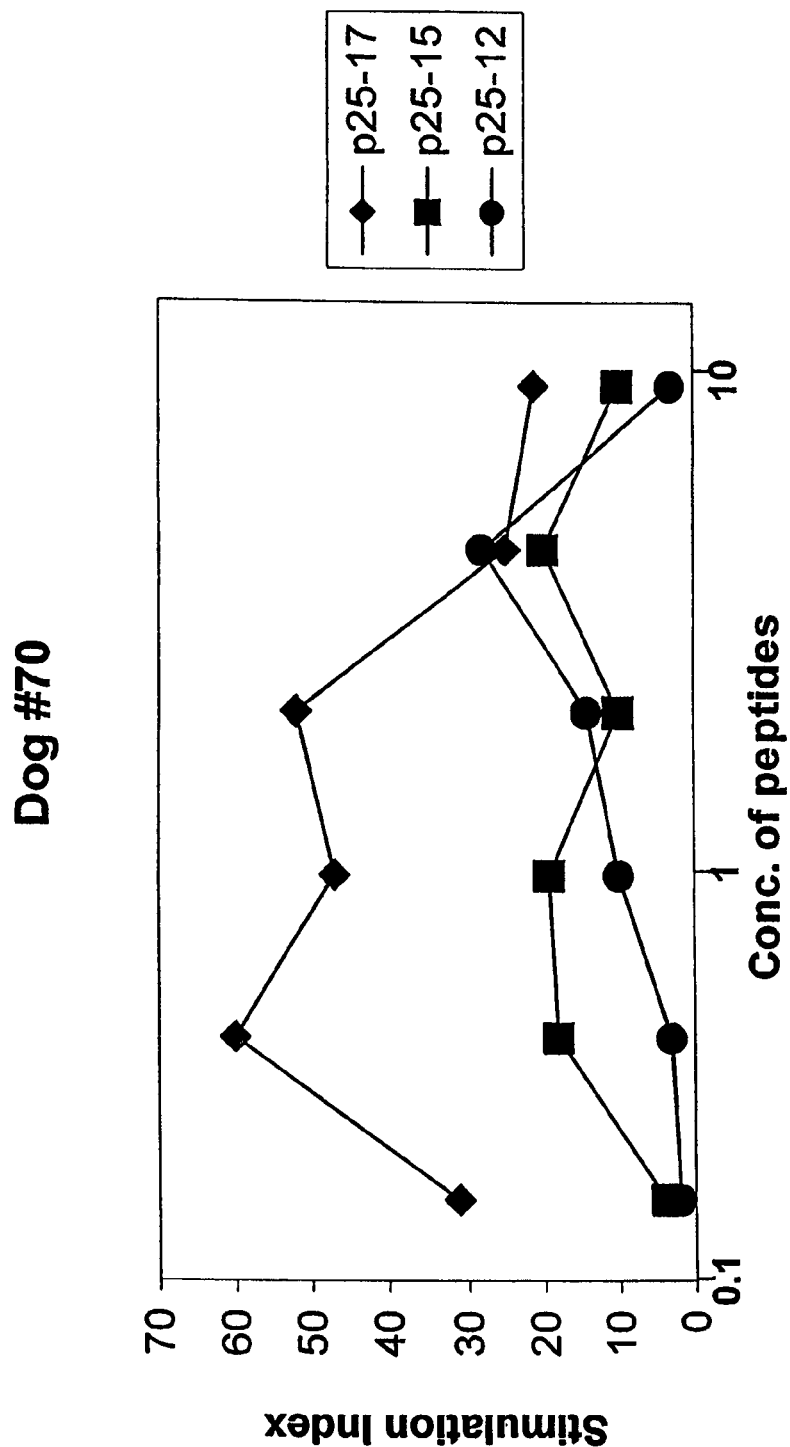
Figure 2B:
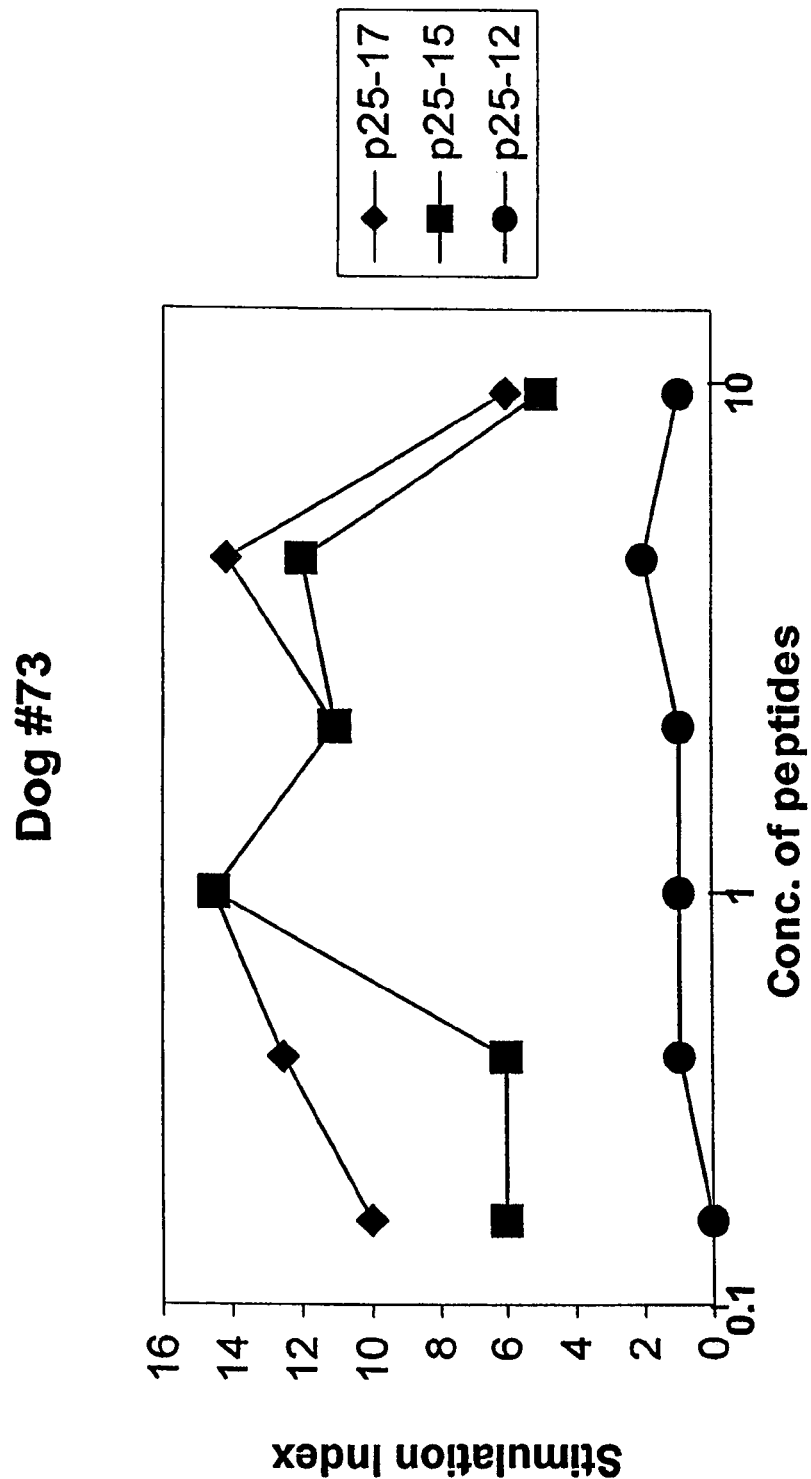

Barrett et al, "The nucleotide sequence of the gene encoding . . . ," Virus Research, vol. 8, pp. 373-386 (1987).

Liermann et al, "Genetic Analysis of the Central Untranslated . . . ," Virus Genes, vol. 17, No. 3, pp. 259-270 (1998).

Bolt et al, "Nucleotide and deducted amino acid sequences . . . ," Virus Research, vol. 34, pp. 291-304 (1994).

Partidos et al, Journal of General Virology, vol. 71, pp. 2009-2105 (1990).

```
  1 MHRGIPKSSK TQTHTQQDRP PQPSTELEET RTSRARHSTT SAQRSTHYDP
 51 RTSDRPVSYT MNRTRSRKQT SHRLKNIPVH GNHEATIQHI PESVSKGARS
101 QIERRQPNAI NSGSHCTWLV LWCLGMASLF LCSKAQIHWD NLSTIGIIGT
151 DNVHYKIMTR PSHQYLVIKL IPNASLIENC TKAELGEYEK LLNSVLEPIN
201 QALTLMTKNV KPLQSLGSGR RQRRFAGVVL AGVALGVATA AQITAGIALH
251 QSNLNAQAIQ SLRTSLEQSN KAIEEIREAT QETVIAVQGV QDYVNNELVP
301 AMQHMSCELV GQRLGLRLLR YYTELLSIFG PSLRDPISAE ISIQALIYAL
351 GGEIHKILEK LGYSGSDMIA ILESRGIKTK ITHVDLPGKF IILSISYPTL
401 SEVKGVIVHR LEAVSYNIGS QEWYTVPRY IATNGYLISN FDESSCVFVS
451 ESAICSQNSL YPMSPLLQQC IRGDTSSCAR TLVSGTMGNK FILSKGNIVA
501 NCASILCKCY STSTIINQSP DKLLTFIASD TCPLVEIDGA TIQVGGRQYP
551 DMVYEGKVAL GPAISLDRLD VGTNLGNALK KLDDAKVLID SSNQILETVR
601 RSSFNFGSLL SVPILSCTAL ALLLLIYCCK RRYQQTLKQH TKVDPAFKPD
651 LTGTSKSYVR SL
```

Figure 1

SEQUENCE LISTING

<160> NUMBER OF SEQ ID NOS: 30

<210> SEQ ID NO 1
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P2

<400> SEQUENCE: 1

Ser Ser Lys Thr Gln Thr His Thr Gln Gln Asp Arg Pro Pro Gln Pro
1               5                   10                  15

Ser

<210> SEQ ID NO 2
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P4

<400> SEQUENCE: 2

Gln Pro Ser Thr Glu Leu Glu Glu Thr Arg Thr Ser Arg Ala Arg His
1               5                   10                  15

Ser

<210> SEQ ID NO 3
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P6

<400> SEQUENCE: 3

Arg His Ser Thr Thr Ser Ala Gln Arg Ser Thr His Tyr Asp Pro Arg
1               5                   10                  15

Thr

<210> SEQ ID NO 4

```
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P8

<400> SEQUENCE: 4

Pro Arg Thr Ser Asp Arg Pro Val Ser Tyr Thr Met Asn Arg Thr Arg
1               5                   10                  15

Ser

<210> SEQ ID NO 5
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P10

<400> SEQUENCE: 5

Thr Arg Ser Arg Lys Gln Thr Ser His Arg Leu Lys Asn Ile Pro Val
1               5                   10                  15

His

<210> SEQ ID NO 6
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P24

<400> SEQUENCE: 6

Ser His Gln Tyr Leu Val Ile Lys Leu Ile Pro Asn Ala Ser Leu Ile
1               5                   10                  15

Glu

<210> SEQ ID NO 7
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P22

<400> SEQUENCE: 7

Ile Gly Thr Asp Asn Val His Tyr Lys Ile Met Thr Arg Pro Ser His
1               5                   10                  15

Gln

<210> SEQ ID NO 8
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P23

<400> SEQUENCE: 8

Tyr Lys Ile Met Thr Arg Pro Ser His Gln Tyr Leu Val Ile Lys Leu
```

-continued

```
                1               5                  10                  15
Ile

<210> SEQ ID NO 9
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P25

<400> SEQUENCE: 9

Lys Leu Ile Pro Asn Ala Ser Leu Ile Glu Asn Cys Thr Lys Ala Glu
1               5                   10                  15
Leu

<210> SEQ ID NO 10
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P27

<400> SEQUENCE: 10

Ala Glu Leu Gly Glu Tyr Glu Lys Leu Leu Asn Ser Val Leu Glu Pro
1               5                   10                  15
Ile

<210> SEQ ID NO 11
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P28

<400> SEQUENCE: 11

Lys Leu Leu Asn Ser Val Leu Glu Pro Ile Asn Gln Ala Leu Thr Leu
1               5                   10                  15
Met

<210> SEQ ID NO 12
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P29

<400> SEQUENCE: 12

Glu Pro Ile Asn Gln Ala Leu Thr Leu Met Thr Lys Asn Val Lys Pro
1               5                   10                  15
Leu

<210> SEQ ID NO 13
<211> LENGTH: 17
<212> TYPE: PRT
<213> ORGANISM: canine distemper virus
<220> FEATURE:
<221> NAME/KEY: misc_feature
```

```
<223> OTHER INFORMATION: synthetic peptide from canine distemper virus
      fusion protein (CDV-F) designated peptide P33

<400> SEQUENCE: 13

Phe Ala Gly Val Val Leu Ala Gly Val Ala Leu Gly Val Ala Thr Ala
1               5                   10                  15

Ala

<210> SEQ ID NO 14
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P34

<400> SEQUENCE: 14

Gly Val Ala Leu Gly Val Ala Thr Ala Ala Gln Ile Thr Ala Gly Ile
1               5                   10                  15

Ala

<210> SEQ ID NO 15
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P35

<400> SEQUENCE: 15

Thr Ala Ala Gln Ile Thr Ala Gly Ile Ala Leu His Gln Ser Asn Leu
1               5                   10                  15

Asn

<210> SEQ ID NO 16
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P36

<400> SEQUENCE: 16

Gly Ile Ala Leu His Gln Ser Asn Leu Asn Ala Gln Ala Ile Gln Ser
1               5                   10                  15

Leu

<210> SEQ ID NO 17
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P37

<400> SEQUENCE: 17

Asn Leu Asn Ala Gln Ala Ile Gln Ser Leu Arg Thr Ser Leu Glu Gln
1               5                   10                  15

Ser
```

```
<210> SEQ ID NO 18
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P38

<400> SEQUENCE: 18

Gln Ser Leu Arg Thr Ser Leu Glu Gln Ser Asn Lys Ala Ile Glu Glu
1               5                   10                  15

Ile

<210> SEQ ID NO 19
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P39

<400> SEQUENCE: 19

Glu Gln Ser Asn Lys Ala Ile Glu Glu Ile Arg Glu Ala Thr Gln Glu
1               5                   10                  15

Thr

<210> SEQ ID NO 20
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P47

<400> SEQUENCE: 20

Thr Glu Leu Leu Ser Ile Phe Gly Pro Ser Leu Arg Asp Pro Ile Ser
1               5                   10                  15

Ala

<210> SEQ ID NO 21
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P62

<400> SEQUENCE: 21

Pro Arg Tyr Ile Ala Thr Asn Gly Tyr Leu Ile Ser Asn Phe Asp Glu
1               5                   10                  15

Ser

<210> SEQ ID NO 22
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P68

<400> SEQUENCE: 22
```

```
Cys Ile Arg Gly Asp Thr Ser Ser Cys Ala Arg Thr Leu Val Ser Gly
1               5                   10                  15

Thr

<210> SEQ ID NO 23
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P64

<400> SEQUENCE: 23

Asp Glu Ser Ser Cys Val Phe Val Ser Glu Ser Ala Ile Cys Ser Gln
1               5                   10                  15

Asn

<210> SEQ ID NO 24
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P74

<400> SEQUENCE: 24

Thr Ser Thr Ile Ile Asn Gln Ser Pro Asp Lys Leu Leu Thr Phe Ile
1               5                   10                  15

Ala

<210> SEQ ID NO 25
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P75

<400> SEQUENCE: 25

Ser Pro Asp Lys Leu Leu Thr Phe Ile Ala Ser Asp Thr Cys Pro Leu
1               5                   10                  15

Val

<210> SEQ ID NO 26
<211> LENGTH: 17
<212> TYPE: PRT
<213> ORGANISM: canine distemper virus
<220> FEATURE:
<221> NAME/KEY: misc_feature
<223> OTHER INFORMATION: synthetic peptide from canine distemper virus
      fusion protein (CDV-F) designated peptide P32

<400> SEQUENCE: 26

Ser Gly Arg Arg Gln Arg Arg Phe Ala Gly Val Val Leu Ala Gly Val
1               5                   10                  15

Ala

<210> SEQ ID NO 27
<211> LENGTH: 662
<212> TYPE: PRT
<213> ORGANISM: canine distemper virus
<220> FEATURE:
```

<221> NAME/KEY: misc_feature
<223> OTHER INFORMATION: canine distemper virus fusion protein (CDV-F)

<400> SEQUENCE: 27

```
Met His Arg Gly Ile Pro Lys Ser Ser Lys Thr Gln Thr His Thr Gln
1               5                   10                  15

Gln Asp Arg Pro Pro Gln Pro Ser Thr Glu Leu Glu Glu Thr Arg Thr
            20                  25                  30

Ser Arg Ala Arg His Ser Thr Thr Ser Ala Gln Arg Ser Thr His Tyr
        35                  40                  45

Asp Pro Arg Thr Ser Asp Arg Pro Val Ser Tyr Thr Met Asn Arg Thr
    50                  55                  60

Arg Ser Arg Lys Gln Thr Ser His Arg Leu Lys Asn Ile Pro Val His
65                  70                  75                  80

Gly Asn His Glu Ala Thr Ile Gln His Ile Pro Glu Ser Val Ser Lys
                85                  90                  95

Gly Ala Arg Ser Gln Ile Glu Arg Arg Gln Pro Asn Ala Ile Asn Ser
            100                 105                 110

Gly Ser His Cys Thr Trp Leu Val Leu Trp Cys Leu Gly Met Ala Ser
        115                 120                 125

Leu Phe Leu Cys Ser Lys Ala Gln Ile His Trp Asp Asn Leu Ser Thr
    130                 135                 140

Ile Gly Ile Ile Gly Thr Asp Asn Val His Tyr Lys Ile Met Thr Arg
145                 150                 155                 160

Pro Ser His Gln Tyr Leu Val Ile Lys Leu Ile Pro Asn Ala Ser Leu
                165                 170                 175

Ile Glu Asn Cys Thr Lys Ala Glu Leu Gly Glu Tyr Glu Lys Leu Leu
            180                 185                 190

Asn Ser Val Leu Glu Pro Ile Asn Gln Ala Leu Thr Leu Met Thr Lys
        195                 200                 205

Asn Val Lys Pro Leu Gln Ser Leu Gly Ser Gly Arg Arg Gln Arg Arg
    210                 215                 220

Phe Ala Gly Val Val Leu Ala Gly Val Ala Leu Gly Val Ala Thr Ala
225                 230                 235                 240

Ala Gln Ile Thr Ala Gly Ile Ala Leu His Gln Ser Asn Leu Asn Ala
                245                 250                 255

Gln Ala Ile Gln Ser Leu Arg Thr Ser Leu Glu Gln Ser Asn Lys Ala
            260                 265                 270

Ile Glu Glu Ile Arg Glu Ala Thr Gln Glu Thr Val Ile Ala Val Gln
        275                 280                 285

Gly Val Gln Asp Tyr Val Asn Asn Glu Leu Val Pro Ala Met Gln His
    290                 295                 300

Met Ser Cys Glu Leu Val Gly Gln Arg Leu Gly Leu Arg Leu Leu Arg
305                 310                 315                 320

Tyr Tyr Thr Glu Leu Leu Ser Ile Phe Gly Pro Ser Leu Arg Asp Pro
                325                 330                 335

Ile Ser Ala Glu Ile Ser Ile Gln Ala Leu Ile Tyr Ala Leu Gly Gly
            340                 345                 350

Glu Ile His Lys Ile Leu Glu Lys Leu Gly Tyr Ser Gly Ser Asp Met
        355                 360                 365

Ile Ala Ile Leu Glu Ser Arg Gly Ile Lys Thr Lys Ile Thr His Val
    370                 375                 380

Asp Leu Pro Gly Lys Phe Ile Ile Leu Ser Ile Ser Tyr Pro Thr Leu
385                 390                 395                 400
```

```
Ser Glu Val Lys Gly Val Ile Val His Arg Leu Glu Ala Val Ser Tyr
            405                 410                 415
Asn Ile Gly Ser Gln Glu Trp Tyr Thr Thr Val Pro Arg Tyr Ile Ala
            420                 425                 430
Thr Asn Gly Tyr Leu Ile Ser Asn Phe Asp Glu Ser Ser Cys Val Phe
            435                 440                 445
Val Ser Glu Ser Ala Ile Cys Ser Gln Asn Ser Leu Tyr Pro Met Ser
        450                 455                 460
Pro Leu Gln Gln Cys Ile Arg Gly Asp Thr Ser Ser Cys Ala Arg
465                 470                 475                 480
Thr Leu Val Ser Gly Thr Met Gly Asn Lys Phe Ile Leu Ser Lys Gly
                485                 490                 495
Asn Ile Val Ala Asn Cys Ala Ser Ile Leu Cys Lys Cys Tyr Ser Thr
                500                 505                 510
Ser Thr Ile Ile Asn Gln Ser Pro Asp Lys Leu Leu Thr Phe Ile Ala
            515                 520                 525
Ser Asp Thr Cys Pro Leu Val Glu Ile Asp Gly Ala Thr Ile Gln Val
        530                 535                 540
Gly Gly Arg Gln Tyr Pro Asp Met Val Tyr Glu Gly Lys Val Ala Leu
545                 550                 555                 560
Gly Pro Ala Ile Ser Leu Asp Arg Leu Asp Val Gly Thr Asn Leu Gly
                565                 570                 575
Asn Ala Leu Lys Lys Leu Asp Asp Ala Lys Val Leu Ile Asp Ser Ser
            580                 585                 590
Asn Gln Ile Leu Glu Thr Val Arg Arg Ser Ser Phe Asn Phe Gly Ser
            595                 600                 605
Leu Leu Ser Val Pro Ile Leu Ser Cys Thr Ala Leu Ala Leu Leu Leu
        610                 615                 620
Leu Ile Tyr Cys Cys Lys Arg Arg Tyr Gln Gln Thr Leu Lys Gln His
625                 630                 635                 640
Thr Lys Val Asp Pro Ala Phe Lys Pro Asp Leu Thr Gly Thr Ser Lys
                645                 650                 655
Ser Tyr Val Arg Ser Leu
            660

<210> SEQ ID NO 28
<211> LENGTH: 10
<212> TYPE: PRT
<213> ORGANISM: Homo sapiens
<220> FEATURE:
<221> NAME/KEY: misc_feature
<223> OTHER INFORMATION: synthetic peptide consisting of amino acid
      residues 1-10 of leuteinising hormone releasing hormone
      (LHRH 1-10)

<400> SEQUENCE: 28

Glu His Trp Ser Tyr Gly Leu Arg Pro Gly
1               5                   10

<210> SEQ ID NO 29
<211> LENGTH: 9
<212> TYPE: PRT
<213> ORGANISM: Homo sapiens
<220> FEATURE:
<221> NAME/KEY: misc_feature
<223> OTHER INFORMATION: synthetic peptide consisting of amino acid
      residues 2-10 of leuteinising hormone releasing hormone
      (LHRH 2-10)
```

-continued

```
<400> SEQUENCE: 29

His Trp Ser Tyr Gly Leu Arg Pro Gly
1               5

<210> SEQ ID NO 30
<211> LENGTH: 27
<212> TYPE: PRT
<213> ORGANISM: Artificial
<220> FEATURE:
<223> OTHER INFORMATION: synthetic control peptide

<400> SEQUENCE: 30

Ala Leu Asn Asn Arg Phe Gln Ile Lys Gly Val Glu Leu Lys Ser Asn
1               5                   10                  15

Ala Asn Pro Asn Ala Asn Pro Asn Ala Asn Pro
            20                  25
```

US 7,572,454 B2

T HELPER CELL EPITOPES

RELATED APPLICATION DATA

This application is a Continuation of U.S. Ser. No. 11/417,131 filed May 4, 2006, now issued as U.S. Pat. No. 7,241,448, which is a divisional patent application of U.S. Ser. No. 10/705,819 filed on Nov. 13, 2003 and now issued as U.S. Pat. No 7,097,844, which is a divisional patent application of U.S. Ser. No. 09/890,650 filed Mar. 22, 2002 and now issued as U.S. Pat. No. 6,685,947, which is a 371 of International Patent Application No. PCT/AU00/00070 filed on Feb. 7, 2000, which claims benefit of foreign priority under 35 USC §119 from Australian Patent Application No. PP8533 filed on Feb. 5, 1999 and Australian Patent Application No. PQ2013 filed on Aug. 4, 1999. The contents of U.S. Ser. No. 11/417,131 filed May 4, 2006, U.S. Ser. No. 10/705,819 (U.S. Pat. No. 7,097,844) filed on Nov. 13, 2003 and U.S. Ser. No. 09/890,650 (U.S. Pat. No. 6,685,947) filed Mar. 22, 2002 are each incorporated in their entirety by reference.

FIELD OF THE INVENTION

The present invention relates to T helper cell epitopes derived from Canine Distemper Virus (CDV). The present invention relates to compositions including at least one T helper cell epitope and optionally B cell epitopes and/or CTL epitopes.

BACKGROUND OF THE INVENTION

For any peptide to be able to induce an effective antibody response it must contain particular sequences of amino acids known as epitopes that are recognised by the immune system. In particular, for antibody responses, epitopes need to be recognised by specific immunoglobulin (Ig) receptors present on the surface of B lymphocytes. It is these cells which ultimately differentiate into plasma cells capable of producing antibody specific for that epitope. In addition to these B cell epitopes, the immunogen must also contain epitopes that are presented by antigen presenting cells (APC) to specific receptors present on helper T lymphocytes, the cells which are necessary to provide the signals required for the B cells to differentiate into antibody producing cells.

In the case of viral infections and in many cases of cancer, antibody is of limited benefit in recovery and the immune system responds with cytotoxic T cells (CTL) which are able to kill the virus-infected or cancer cell. Like helper T cells, CTL are first activated by interaction with APC bearing their specific peptide epitope presented on the surface, this time in association with MHC class I rather than class II molecules. Once activated the CTL can engage a target cell bearing the same peptide/class I complex and cause its lysis. It is also becoming apparent that helper T cells play a role in this process; before the APC is capable of activating the CTL it must first receive signals from the helper T cell to upregulate the expression of the necessary costimulatory molecules.

Helper T cell epitopes are bound by molecules present on the surface of APCs that are coded by class II genes of the major histocompatibility complex (MHC). The complex of the class II molecule and peptide epitope is then recognised by specific T-cell receptors (TCR) on the surface of T helper lymphocytes. In this way the T cell, presented with an antigenic epitope in the context of an MHC molecule, can be activated and provide the necessary signals for the B lymphocyte to differentiate. Traditionally the source of helper T cell epitopes for a peptide immunogen is a carrier protein to which peptides are covalently coupled but this coupling procedure can introduce other problems such as modification of the antigenic determinant during the coupling process and the induction of antibodies against the carrier at the expense of antibodies which are directed toward the peptide (Schutze, M. P., Leclerc, C. Jolivet, M. Audibert, F. Chedid, L. Carrier-induced epitopic suppression, a major issue for future synthetic vaccines. J Immunol. 1985, 135, 2319-2322; DiJohn, D., Torrese, J. R. Murillo, J. Herrington, D. A. et al. Effect of priming with carrier on response to conjugate vaccine. The Lancet. 1989, 2, 1415-1416). Furthermore, the use of irrelevant proteins in the preparation introduces issues of quality control. The choice of appropriate carrier proteins is very important in designing peptide vaccines and their selection is limited by factors such as toxicity and feasibility of their large scale production. There are other limitations to this approach including the size of the peptide load that can be coupled and the dose of carrier that can be safely administered (Audibert, F. a. C., L. 1984. Modem approaches to vaccines. Molecular and chemical basis of virus virulence and immunogenicity., Cold Spring Harbor Laboratory, New York.). Although carrier molecules allow the induction of a strong immune response they are also associated with undesirable effects such as suppression of the anti-peptide antibody response (Herzenberg, L. A. and Tokuhisa, T. 1980. Carrier-priming leads to hapten-specific suppression. Nature 285:664; Schutze, M. P., Leclerc, C., Jolivet, M., Audibert, F., and Chedid, L. 1985. Carrier-induced epitopic suppression, a major issue for future synthetic vaccines. J Immunol 135:2319; Etlinger, H. M., Felix, A. M., Gillessen, D., Heimer, E. P., Just, M., Pink, J. R., Sinigaglia, F., Sturchler, D., Takacs, B., Trzeciak, A., and et, a. 1988. Assessment in humans of a synthetic peptide-based vaccine against the sporozoite stage of the human malaria parasite, Plasmodium falciparum. J Immunol 140:626).

In general then, an immunogen must contain epitopes capable of being recognised by helper T cells in addition to the epitopes that will be recognised by surface Ig or by the receptors present on cytotoxic T cells. It should be realised that these types of epitopes may be very different. For B cell epitopes, conformation is important as the B cell receptor binds directly to the native immunogen. In contrast, epitopes recognised by T cells are not dependent on conformational integrity of the epitope and consist of short sequences of approximately nine amino acids for CTL and slightly longer sequences, with less restriction on length, for helper T cells. The only requirements for these epitopes are that they can be accommodated in the binding cleft of the class I or class II molecule respectively and that the complex is then able to engage the T-cell receptor. The class II molecule's binding site is open at both ends allowing a much greater variation in the length of the peptides bound (Brown, J. H., T. S. Jardetzky, J. C. Gorga, L. J. Stem, R. G. Urban, J. L. Strominger and D. C. Wiley. 1993. Three-dimensional structure of the human class II histocompatibility antigen HLA-DR1. Nature 364:33) with epitopes as short as 8 amino acid residues being reported (Fahrer, A. M., Geysen, H. M., White, D. O., Jackson, D. C. and Brown, L. E. Analysis of the requirements for class II-restricted T-cell recognition of a single determinant reveals considerable diversity in the T-cell response and degeneracy of peptide binding to I-Ed J. Immunol. 1995. 155: 2849-2857).

Canine distemper virus (CDV) belongs to the subgroup of morbillivirus of paramyxovirus family of negative-stranded RNA viruses. Other viruses which are members of this group are measles virus and rinderpest virus. Development of peptide based vaccines has aroused considerable interest in identification of B and T cell epitopes from sequences of proteins.

The rationale for using T cell epitopes from proteins such as the F protein of CDV is that young dogs are inoculated against CDV in early life and will therefore possess helper T cells specific for helper T cell epitopes present on this protein. Subsequent exposure to a vaccine which contains one or more of the epitopes will therefore result in recruitment of existing helper T cells and consequently an enhanced immune response. Such helper T cell epitopes could, however, be administered to unprimed animals and still induce an immune response. The present inventors aimed to identify canine T cell epitopes from the sequence of CDV fusion protein so that these epitopes can then be used in the design of peptide based vaccines, in particular, for the canine and related species.

LHRH (Luteinising hormone releasing hormone) is a ten amino acids long peptide hormone whose sequence is conserved in mammals. It is secreted by the hypothalamus and controls the reproductive physiology of both males and females. The principle of development of LHRH-based immunocontraceptive vaccines is based on observations that antibodies to LHRH block the action of the hormone on pituitary secretion of luteinising hormone and follicle stimulating hormone, leading to gonadal atrophy and sterility in mammals.

Most LHRH vaccines that have been developed consist of LHRH chemically conjugated to protein carriers to provide T cell help for the generation of anti-LHRH antibodies. It has been shown that upon repeated inoculation of LHRH-protein carrier conjugates the anti-LHRH titre decreases due to the phenomenon known as "carrier induced epitope suppression". One aim of the present inventors is to replace protein carriers in the vaccines with defined T helper epitopes (TH-epitopes) so as to eliminate "carrier induced epitope suppression".

SUMMARY OF THE INVENTION

The present inventors have identified a number of 17 residue peptides each of which includes a T helper cell epitope. As will be readily appreciated the majority of these peptides are not minimal T helper cell epitopes. Typically class II molecules have been shown to be associated with peptides as short as 8 amino acids (Fahrer et al., 1995 ibid) but usually of 12-19 amino acids (Chicz, R. M., Urban, R. G., Gorga, J. C., Vignali, D. A. A., Lane, W. S. and Strominger, J. L. Specificity and promiscuity among naturally processed peptides bound to HLA-DR alleles. J Exp Med 1993, 178, 27-47; Chicz, R. M., Urban, R. G., Lane, W. S., Gorga, J. C., Stem, L. J., Vignali, D. A. A. and Strominger, J. L. Predominant naturally processed peptides bound to HLA-DR1 are derived from MHC-related molecules and are heterogeneous in size. Nature 1992, 358, 764-8), although, peptides up to 25 amino acids in length have been reported to bind to class II (reviewed in Rammensee, H.-G. Chemistry of peptide associated with class I and class II molecules. Curr. Opin. Immunol. 1995, 7, 85-95.).

Thus peptide epitopes that range in length between 8 and 25 amino acid residues can bind to class II molecules. The shorter peptides are "core" epitopes that may have less activity than longer sequences but it is a trivial exercise to truncate longer sequences at the N- or the C-terminus to yield shorter sequences that have the same or better activity than the parent sequence.

Accordingly in a first aspect the present invention consists in a T helper cell epitope, the epitope being contained within a peptide sequence selected from the group consisting of SSKTQTHTQQDRPPQPS (SEQ ID NO: 1); QPSTELEETRTSRARHS (SEQ ID NO: 2); RHSTTSAQRSTHYDPRT (SEQ ID NO: 3); PRTSDRPVSYTMNRTRS (SEQ ID NO: 4); TRSRKQTSHRLKNIPVH (SEQ ID NO: 5); SHQYLVIKLIPNASLIE (SEQ ID NO: 6); IGTDNVHYKIMTRPSHQ (SEQ ID NO: 7); YKIMTRPSHQYLVIKLI (SEQ ID NO: 8); KLIPNASLIENCTKAEL (SEQ ID NO: 9); AELGEYEKLLNSVLEPI (SEQ ID NO: 10); KLLNSVLEPINQALTLM (SEQ ID NO: 11); EPINQALTLMTKNVKPL (SEQ ID NO: 12); FAGVVLAGVALGVATAA (SEQ ID NO: 13); GVALGVATAAQITAGIA (SEQ ID NO: 14); TAAQITAGIALHQSNLN (SEQ ID NO: 15); GIALHQSNLNAQAIQSL (SEQ ID NO: 16); NLNAQAIQSLRTSLEQS (SEQ ID NO: 17); QSLRTSLEQSNKAIEEI (SEQ ID NO: 18); EQSNKAIEEIREATQET (SEQ ID NO: 19); TELLSIFGPSLRDPISA (SEQ ID NO: 20); PRYIATNGYLISNFDES (SEQ ID NO: 21); CIRGDTSSCARTLVSGT (SEQ ID NO: 22); DESSCVFVSESAICSQN (SEQ ID NO: 23); TSTIINQSPDKLLTFIA (SEQ ID NO: 24), SPDKLLTFIASDTCPLV (SEQ ID NO: 25) and SGRRQRRFAGVVLAGVA (SEQ ID NO: 26).

In a second aspect the present invention consists in a composition for use in raising an immune response in an animal, the composition comprising at least one T helper cell epitope, the at least one T helper cell epitope being contained within a peptide sequence selected from the group consisting of SSKTQTHTQQDRPPQPS (SEQ ID NO: 1); QPSTELEETRTSRARHS (SEQ ID NO: 2); RHSTTSAQRSTHYDPRT (SEQ ID NO: 3); PRTSDRPVSYTMNRTRS (SEQ ID NO: 4); TRSRKQTSHRLKNIPVH (SEQ ID NO: 5); SHQYLVIKLIPNASLIE (SEQ ID NO: 6); IGTDNVHYKIMTRPSHQ (SEQ ID NO: 7); YKIMTRPSHQYLVIKLI (SEQ ID NO: 8); KLIPNASLIENCTKAEL (SEQ ID NO: 9); AELGEYEKLLNSVLEPI (SEQ ID NO: 10); KLLNSVLEPINQALTLM (SEQ ID NO: 11); EPINQALTLMTKNVKPL (SEQ ID NO: 12); FAGVVLAGVALGVATAA (SEQ ID NO: 13); GVALGVATAAQITAGIA (SEQ ID NO: 14); TAAQITAGIALHQSNLN (SEQ ID NO: 15); GIALHQSNLNAQAIQSL (SEQ ID NO: 16); NLNAQAIQSLRTSLEQS (SEQ ID NO: 17); QSLRTSLEQSNKAIEEI (SEQ ID NO: 18); EQSNKAIEEIREATQET (SEQ ID NO: 19); TELLSIFGPSLRDPISA (SEQ ID NO: 20); PRYIATNGYLISNFDES (SEQ ID NO: 21); CIRGDTSSCARTLVSGT (SEQ ID NO: 22); DESSCVFVSESAICSQN (SEQ ID NO: 23); TSTIINQSPDKLLTFIA (SEQ ID NO: 24), SPDKLLTFIASDTCPLV (SEQ ID NO: 25) and SGRRQRRFAGVVLAGVA (SEQ ID NO: 26).

In a preferred embodiment of the present invention the composition comprises at least one peptide selected from the group consisting of SSKTQTHTQQDRPPQPS (SEQ ID NO: 1); QPSTELEETRTSRARHS (SEQ ID NO: 2); RHSTTSAQRSTHYDPRT (SEQ ID NO: 3); PRTSDRPVSYTMNRTRS (SEQ ID NO: 4); TRSRKQTSHRLKNIPVH (SEQ ID NO: 5); SHQYLVIKLIPNASLIE (SEQ ID NO: 6); IGTDNVHYKIMTRPSHQ (SEQ ID NO: 7); YKIMTRPSHQYLVIKLI (SEQ ID NO: 8); KLIPNASLIENCTKAEL (SEQ ID NO: 9); AELGEYEKLLNSVLEPI (SEQ ID NO: 10); KLLNSVLEPINQALTLM (SEQ ID NO: 11); EPINQALTLMTKNVKPL (SEQ ID NO: 12); FAGVVLAGVALGVATAA (SEQ ID NO: 13); GVALGVATAAQITAGIA (SEQ ID NO: 14); TAAQITAGIALHQSNLN (SEQ ID NO: 15); GIALHQSNLNAQAIQSL (SEQ ID NO: 16); NLNAQAIQSLRTSLEQS (SEQ ID NO: 17); QSLRTSLEQSNKAIEEI (SEQ ID NO: 18); EQSNKAIEEIREATQET (SEQ ID NO: 19); TELLSIFGPSLRDPISA (SEQ ID NO: 20); PRYIATNGYLISNFDES (SEQ ID NO: 21); CIRGDTSSCARTLVSGT (SEQ ID NO: 22); DESSCVFVSESAICSQN (SEQ ID NO: 23); TSTIINQSPDKLLTFIA (SEQ ID NO: 24), SPDKLLTFIASDTCPLV (SEQ ID NO: 25) and SGRRQRRFAGVVLAGVA (SEQ ID NO: 26).

It is further preferred that the composition further comprises at least one B cell epitope and/or at least one CTL epitope.

In yet another preferred embodiment the at least one B cell epitope and/or the at least one CTL epitope are linked to at least one of the T helper cell epitopes. It is also preferred that the composition comprises a plurality of epitope constructs in which each comprises at least one T helper cell epitope and at least one B cell epitope. Alternatively the composition may comprises a plurality of epitope constructs in which each comprises at least one T helper cell epitope and at least one CTL epitope.

It will be understood that the B cell epitope or CTL epitope may be any epitope. A currently preferred B cell epitope is an LHRH B cell epitope.

The composition of the present invention may comprises a plurality of T helper cell epitopes. These epitopes may be singular or be linked together to form a single polypeptide. It will be understood that where the epitopes are linked to together in a single polypeptide the epitopes may be contiguous or spaced apart by additional amino acids which are not themselves part of the T helper cell epitopes.

As discussed above in one embodiment the T helper cell epitopes and at least one B cell epitope and/or at least one CTL epitope in which the epitopes are linked. This may be done by simple covalent linkage of the peptides. In another embodiment the epitopes are polymerised, most preferably such as described in PCT/AU98/00076, the disclosure of which is incorporated herein by reference.

In yet another preferred embodiment the composition further comprises a pharmaceutically acceptable excipient, preferably an adjuvant.

In a further aspect the present invention consists in a method of inducing an immune response in an animal, the method comprising administering to the animal the composition of the second aspect of the present invention.

Pharmaceutically acceptable carriers or diluents include those used in compositions suitable for oral, rectal, nasal, topical (including buccal and sublingual), vaginal, parenteral (including subcutaneous, intramuscular, intravenous, intradermal, intrathecal and epidural) administration. They are nontoxic to recipients at the dosages and concentrations employed. Representative examples of pharmaceutically acceptable carriers or diluents include, but are not limited to, water, isotonic solutions which are preferably buffered at a physiological pH (such as phosphate-buffered saline or Tris-buffered saline) and can also contain one or more of, mannitol, lactose, trehalose, dextrose, glycerol, ethanol or polypeptides (such as human serum albumin). The compositions may conveniently be presented in unit dosage form and may be prepared by any of the methods well known in the art of pharmacy.

As mentioned it is preferred that the composition includes an adjuvant. As will be understood an "adjuvant" means a composition comprised of one or more substances that enhances the immunogenicity and efficacy of a vaccine composition. Non-limiting examples of suitable adjuvants include squalane and squalene (or other oils of animal origin); block copolymers; detergents such as Tween®-80; Quil® A, mineral oils such as Drakeol or Marcol, vegetable oils such as peanut oil; Corynebacterium-derived adjuvants such as Corynebacterium parvum; Propionibacterium-derived adjuvants such as Propionibacterium acne; Mycobacterium bovis (Bacille Calmette and Guerin or BCG); interleukins such as interleukin 2 and interleukin 12; monokines such as interleukin 1; tumour necrosis factor; interferons such as gamma interferon; combinations such as saponin-aluminium hydroxide or Quil-A aluminium hydroxide; liposomes; ISCOM adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol' EMA; acrylic copolymer emulsions such as Neocryl A640 (e.g. U.S. Pat. No. 5,047,238); vaccinia or animal poxvirus proteins; sub-viral particle adjuvants such as cholera toxin, or mixtures thereof.

As will be recognised by those skilled in the art modifications may be made to the peptides of the present invention without complete abrogation of biological activity. These modifications include additions, deletions and substitutions, in particular conservative substitutions. It is intended that peptides including such modifications which do not result in complete loss of activity as T helper cell epitopes are within the scope of the present invention.

Whilst the concept of substitution is well known in the field the types of substitutions envisaged are set out below.

| Original Residue | Exemplary Substitutions | Preferred Substitutions |
|---|---|---|
| Ala (A) | val; leu; ile | Val |
| Arg (R) | lys; gln; asn | Lys |
| Asn (N) | gln; his; lys; arg | Gln |
| Asp (D) | Glu | Glu |
| Cys (C) | Ser | Ser |
| Gln (Q) | Asn | asn |
| Glu (E) | Asp | asp |
| Gly (G) | Pro | pro |
| His (H) | asn; gln; lys; arg | arg |
| Ile (I) | leu; val; met; ala; phe, norleucine | leu |
| Leu (L) | norleucine, ile; val; met; ala; phe | ile |
| Lys (K) | arg, gln, asn | arg |
| Met (M) | leu; phe; ile; | leu |
| Phe (F) | leu; val; ile; ala | leu |
| Pro (P) | Gly | gly |
| Ser (S) | Thr | thr |
| Thr (T) | Ser | ser |
| Trp (W) | Tyr | tyr |
| Tyr (Y) | trp; phe; thr; ser | phe |
| Val (V) | ile; leu; met; phe ala; norleucine | leu |

Another type of modification of the peptides envisaged include, but are not limited to, modifications to side chains, incorporation of unnatural amino acids and/or their derivatives during peptide synthesis and the use of crosslinkers and other methods which impose conformational constraints on the peptides.

Examples of side chain modifications contemplated by the present invention include, but are not limited to, modifications of amino groups such as by reductive alkylation by reaction with an aldehyde followed by reduction with $NaBH_4$; amidation with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid; 2-thienyl alanine and/or D-isomers of amino acids.

Figure 2C:
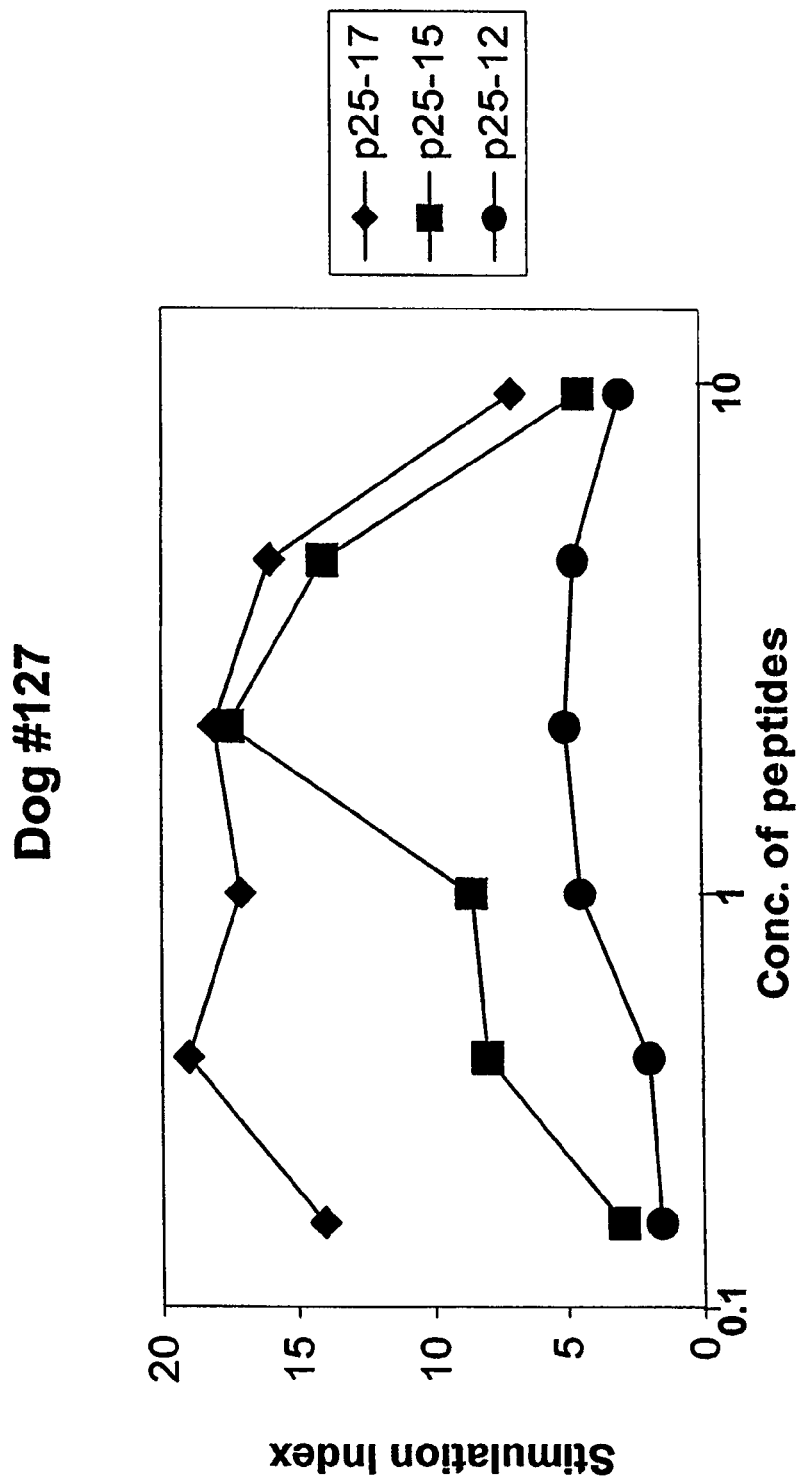

The peptides of the present invention may be derived from CDV. Alternatively, the peptide or combination of peptide epitopes may be produced by recombinant DNA technology. It is, however, preferred that the peptides are produced synthetically using methods well known in the field. For example, the peptides may be synthesised using solution synthesis or solid phase synthesis as described, for example, in Chapter 9 entitled "Peptide Synthesis" by Atherton and Sheppard which is included in a publication entitled "Synthetic Vaccines" edited by Nicholson and published by Blackwell Scientific Publications. Preferably a solid phase support is utilised which may be polystyrene gel beads wherein the polystyrene may be cross-linked with a small proportion of divinylbenzene (e.g. 1%) which is further swollen by lipophilic solvents such as dichloromethane or more polar solvents such as dimethylformamide (DMF). The polystyrene may be functionalised with chloromethyl or aminomethyl groups. Alternatively, cross-linked and functionalised polydimethyl-acrylamide gel is used which may be highly solvated and swollen by DMF and other dipolar aprotic solvents. Other supports can be utilised based on polyethylene glycol which is usually grafted or otherwise attached to the surface of inert polystyrene beads. In a preferred form, use may be made of commercial solid supports or resins which are selected from PAL-PEG-PS, PAC-PEG-PS, KA, KR or TGR.

In solid state synthesis, use is made of reversible blocking groups which have the dual function of masking unwanted reactivity in the α-amino, carboxy or side chain functional groups and of destroying the dipolar character of amino acids and peptides which render them inactive. Such functional groups can be selected from t-butyl esters of the structure RCO—$OCMe_3$—CO. Use may also be made of the corresponding benzyl esters having the structure RCO—$OCH_2$—$C_6H_5$ and urethanes having the structure $C_6H_5CH_2OCO$—NHR which are known as the benzyloxycarbonyl or Z-derivatives and any $Me_3$—COCO—NHR, which are known as t-butoxyl carbonyl, or Boc derivatives. Use may also be made of derivatives of fluorenyl methanol and especially the fluorenyl-methoxy carbonyl or Fmoc group. Each of these types of protecting group is capable of independent cleavage in the presence of one other so that frequent use is made, for example, of BOC-benzyl and Fmoc-tertiary butyl protection strategies.

Reference also should be made to a condensing agent to link the amino and carboxy groups of protected amino acids or peptides. This may be done by activating the carboxy group so that it reacts spontaneously with a free primary or secondary amine. Activated esters such as those derived from p-nitrophenol and pentafluorophenol may be used for this purpose. Their reactivity may be increased by addition of catalysts such as 1-hydroxybenzotriazole. Esters of triazine DHBT (as discussed on page 215-216 of the abovementioned Nicholson reference) also may be used. Other acylating species are formed in situ by treatment of the carboxylic acid (i.e. the N-alpha-protected amino acid or peptide) with a condensing reagent and are reacted immediately with the amino component (the carboxy or C-protected amino acid or peptide). Dicyclohexylcarbodiimide, the BOP reagent (referred to on page 216 of the Nicholson reference), O'Benzotriazole-N,N,N'N'-tetra methyl-uronium hexafluorophosphate (HBTU) and its analogous tetrafluoroborate are frequently used condensing agents.

The attachment of the first amino acid to the solid phase support may be carried out using BOC-amino acids in any suitable manner. In one method BOC amino acids are attached to chloromethyl resin by warming the triethyl ammonium salts with the resin. Fmoc-amino acids may be coupled to the p-alkoxybenzyl alcohol resin in similar manner. Alternatively, use may be made of various linkage agents or "handles" to join the first amino acid to the resin. In this regard, p-hydroxymethyl phenylacetic acid linked to aminomethyl polystyrene may be used for this purpose.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DETAILED DESCRIPTION OF THE INVENTION

In order that the nature of the present invention may be more readily understood preferred forms there of will now be described with reference to the following non-limiting examples.

FIGURE LEGENDS

FIG. 1. Amino acid sequence of the fusion protein of CDV (SEQ ID NO: 27)

FIG. 2*a*. Stimulation indices to Th-epitope P25 and its truncated versions in Dog #70 immunised with P25-LHRH (X-axis concentration of peptides nmoles/well).

FIG. 2*b* Stimulation indices to Th-epitope P25 and its truncated versions in Dog #73 immunised with P25-LHRH (X-axis concentration of peptides nmoles/well).

FIG. 2c Stimulation indices to Th-epitope P25 and its truncated versions in Dog #127 immunised with P25-LHRH (X-axis concentration of peptides nmoles/well).

Figure 2D:
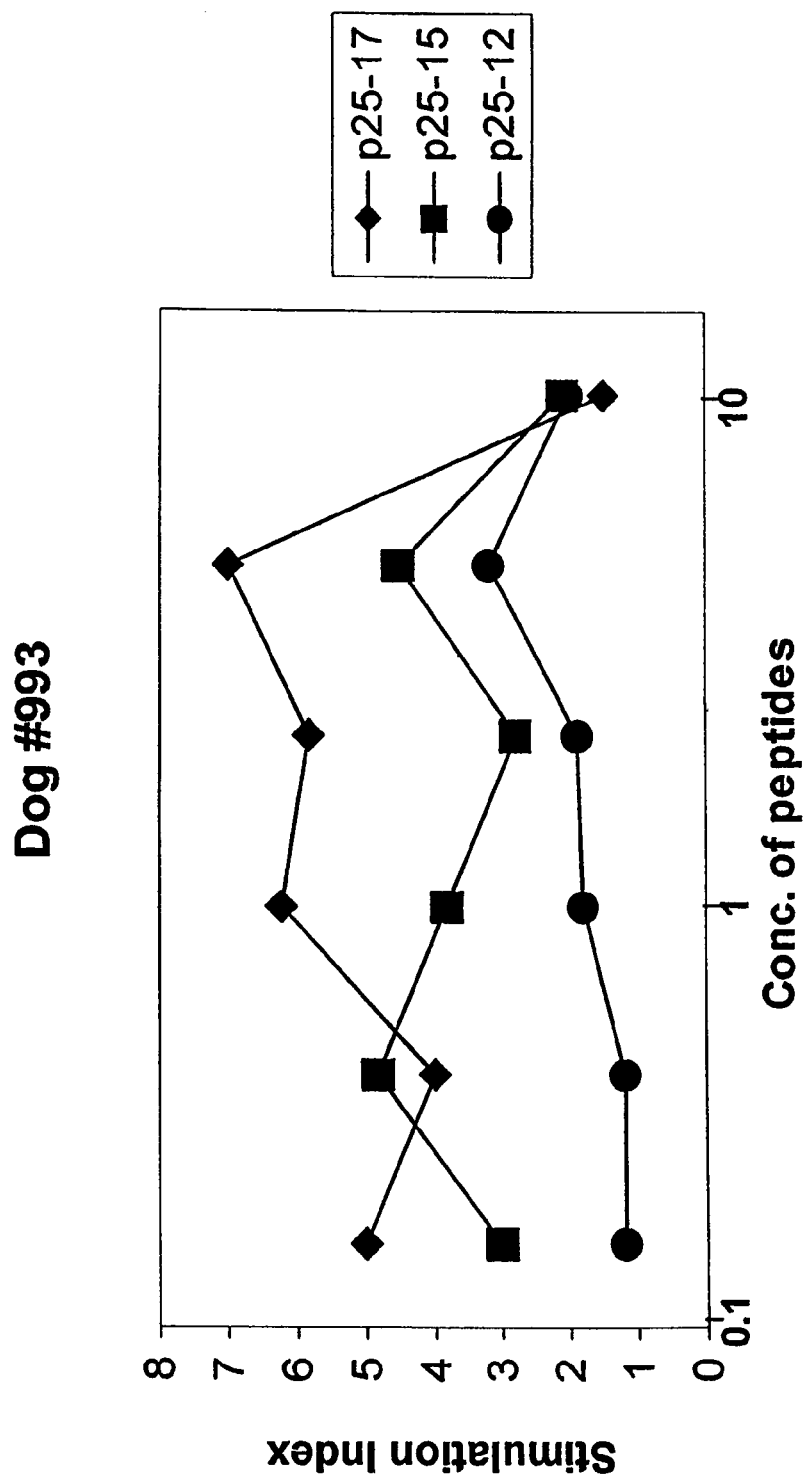

FIG. 2d Stimulation indices to Th-epitope P25 and its truncated versions in Dog #993 immunised with P25-LHRH (X-axis concentration of peptides nmoles/well).

Figure 3A:
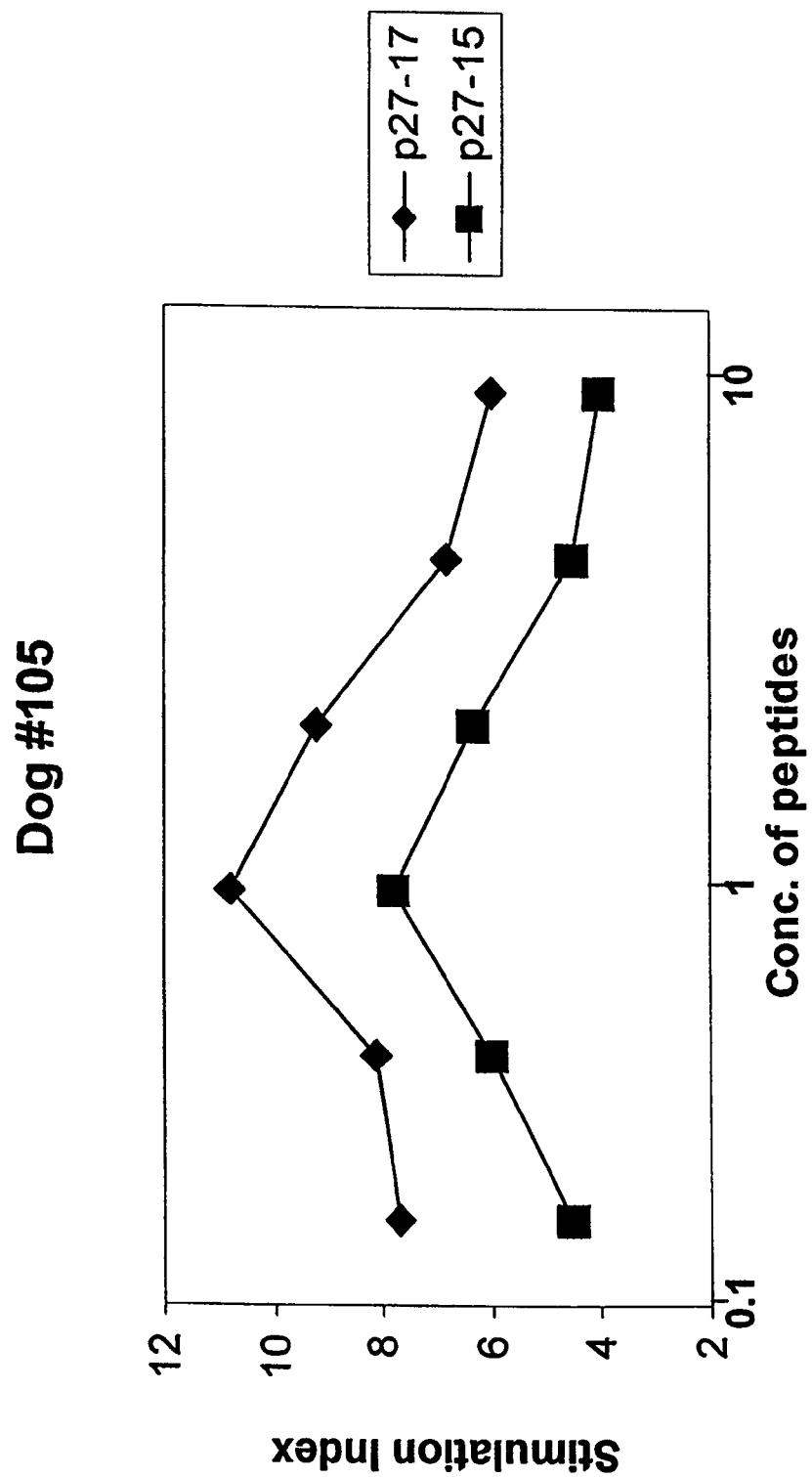

FIG. 3a. Stimulation indices to Th-epitope P27 and its truncated 15-mer in Dog #105 immunised with P27-LHRH. (X-axis concentration of peptides nmoles/well).

Figure 3B:
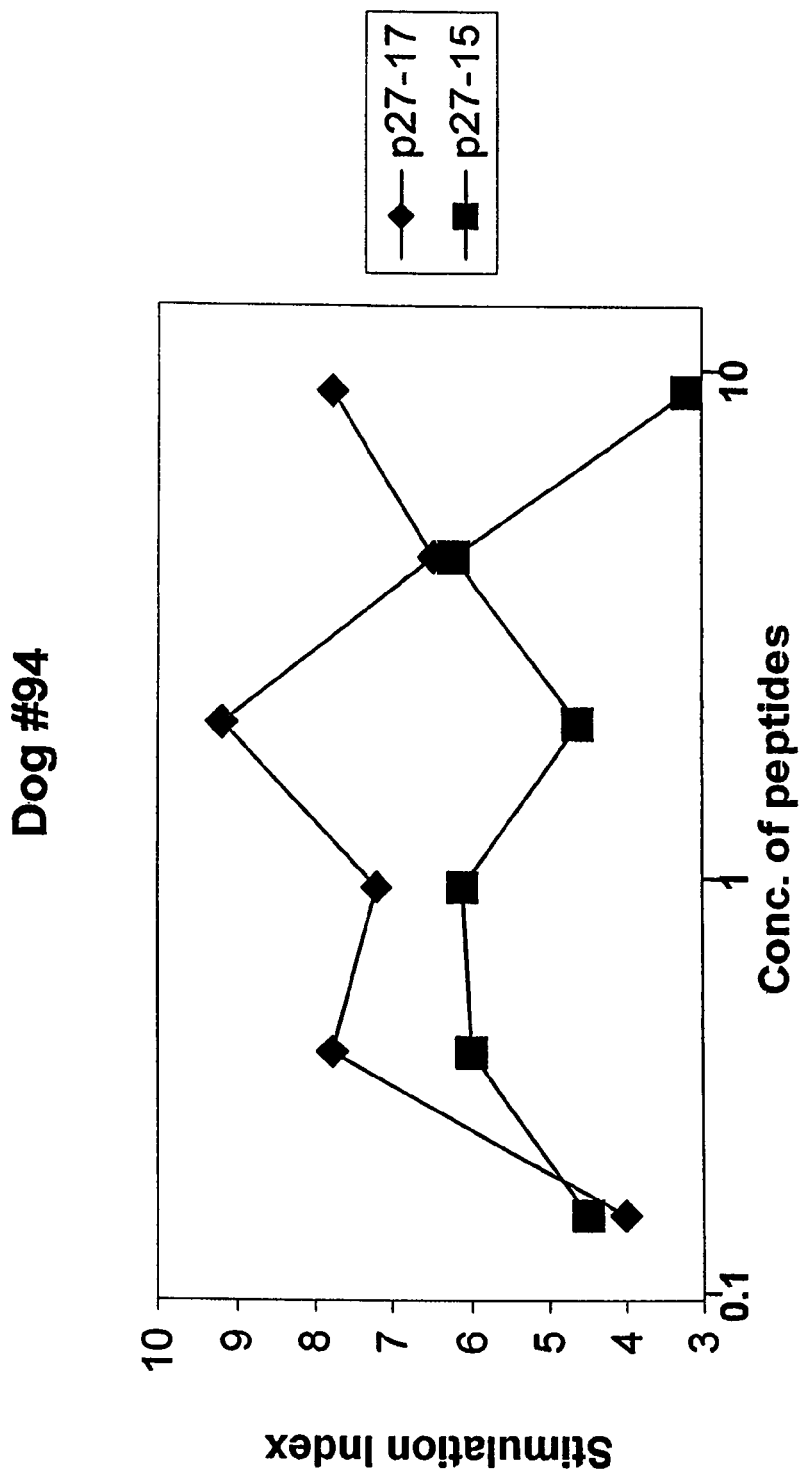

FIG. 3b. Stimulation indices to Th-epitope P27 and its truncated 15-mer in ) Dog #94 immunised with P27-LHRH. (X-axis concentration of peptides nmoles/well).

Figure 3C:
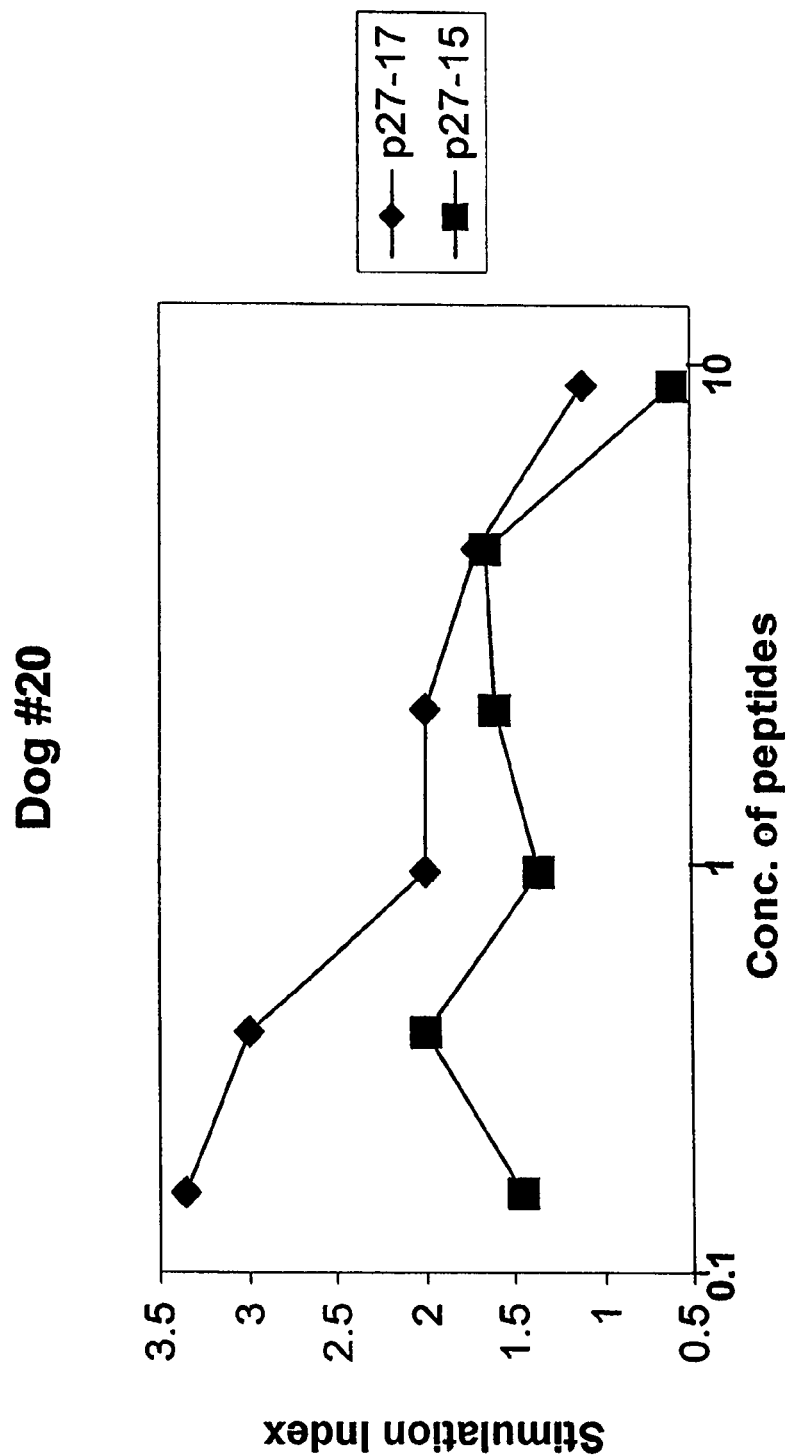

FIG. 3c. Stimulation indices to Th-epitope P27 and its truncated 15-mer in Dog #20 immunised with P27-LHRH. (X-axis concentration of peptides nmoles/well).

Figure 3D:
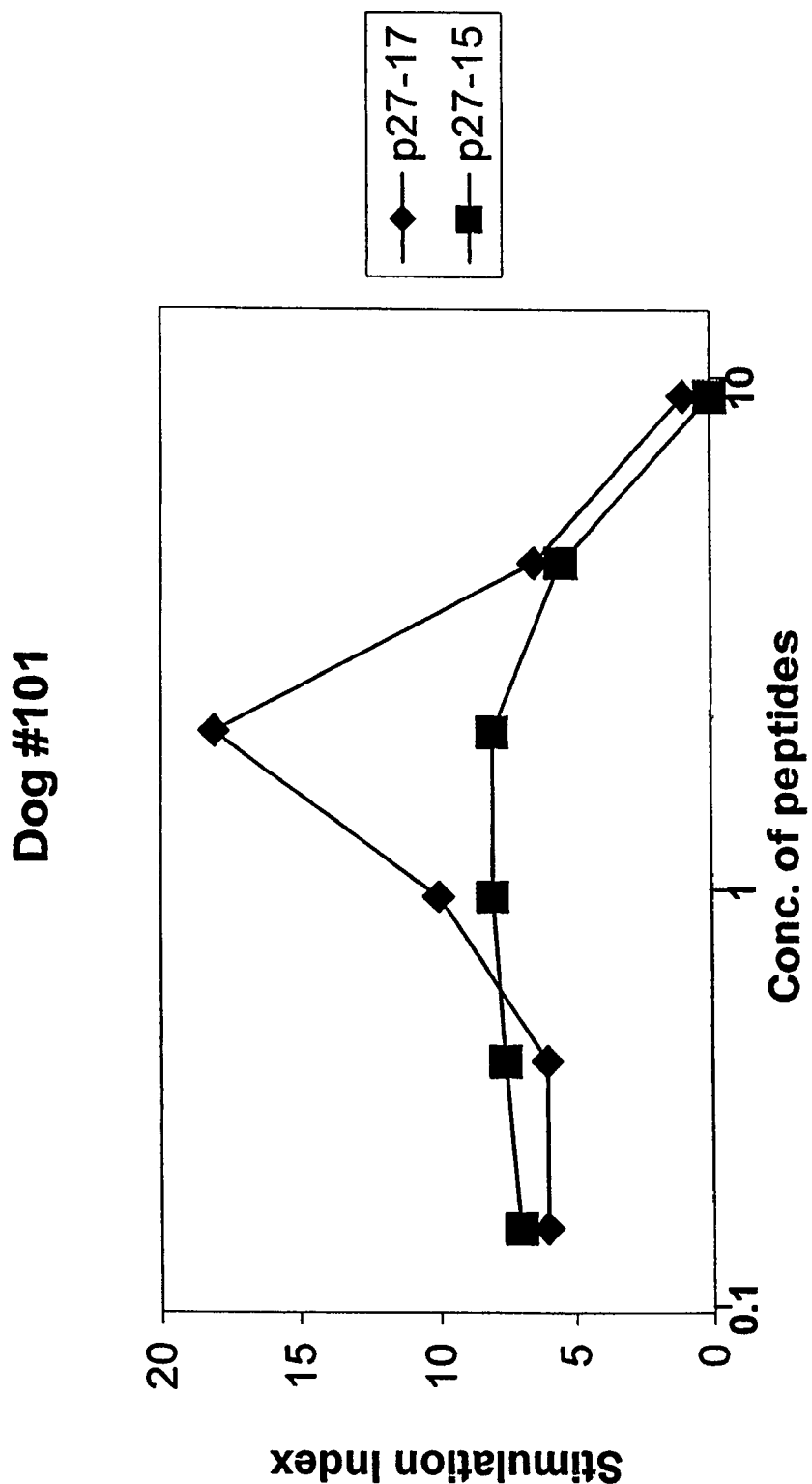

FIG. 3d. Stimulation indices to Th-epitope P27 and its truncated 15-mer in Dog #101 immunised with P27-LHRH. (X-axis concentration of peptides nmoles/well).

Figure 4A:
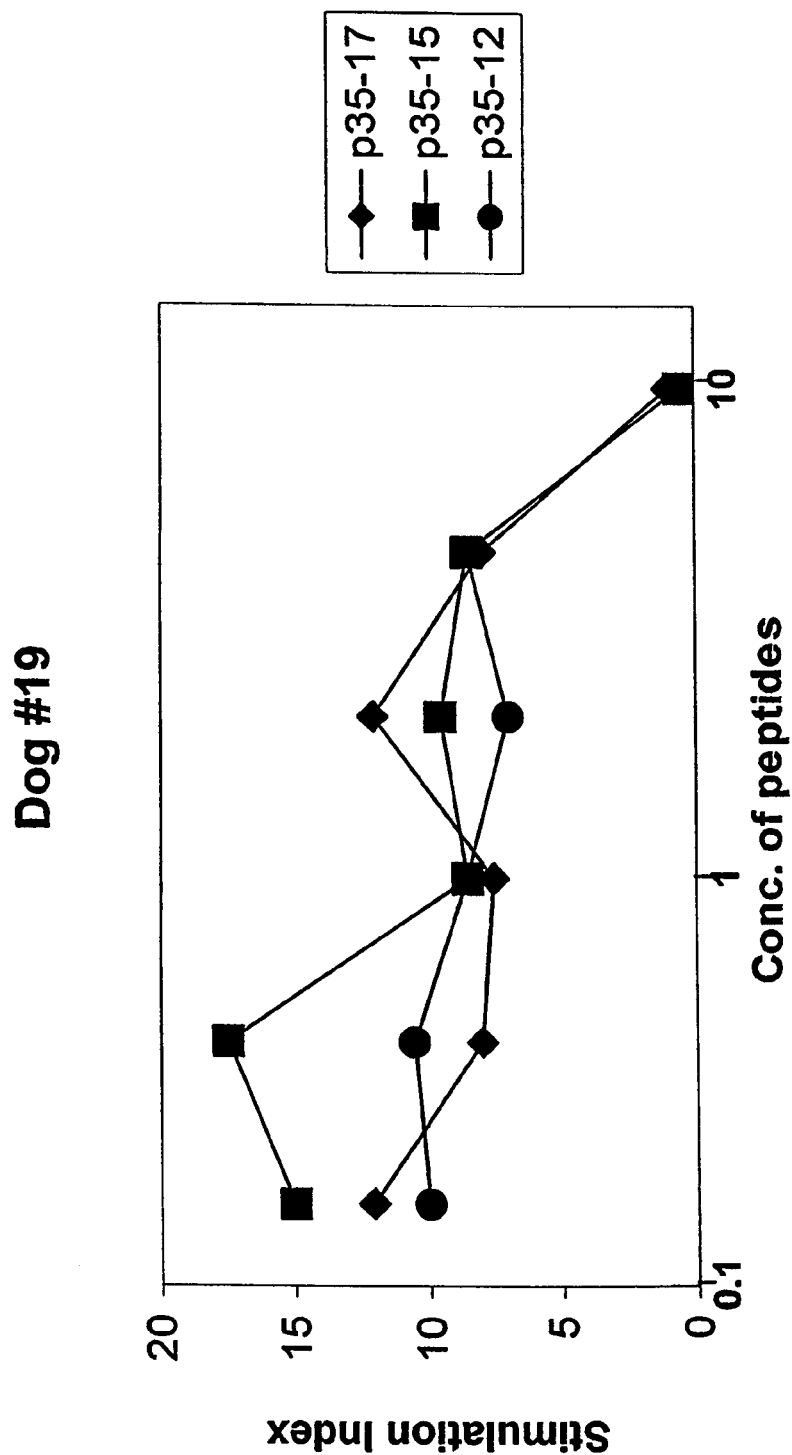

FIG. 4a. Stimulation indices to Th-epitope P35 and its truncated versions in Dog #19 immunised with P35-LHRH (X-axis concentration of peptides nmoles/well).

Figure 4B:
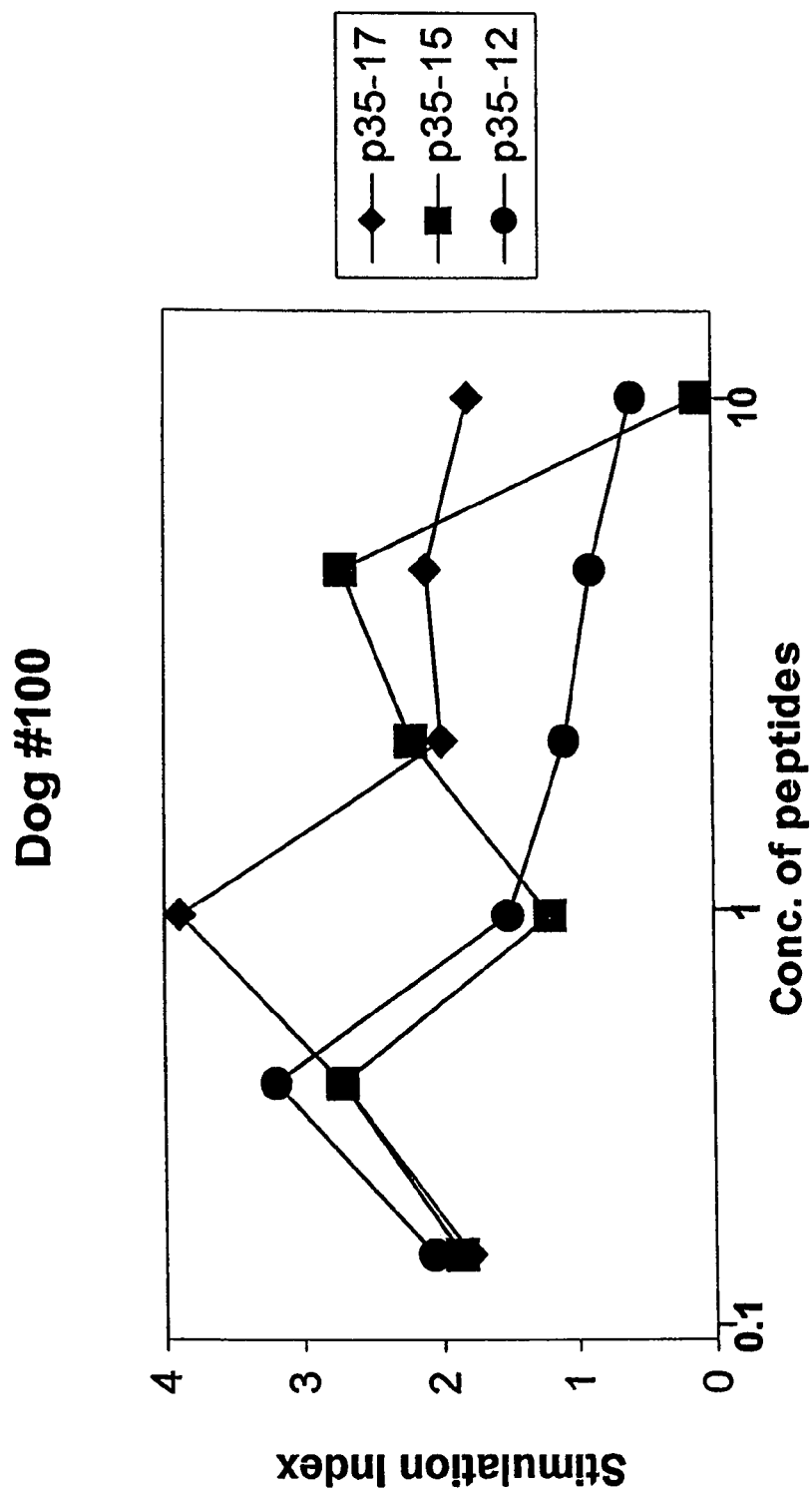

FIG. 4b. Stimulation indices to Th-epitope P35 and its truncated versions in Dog #100 immunised with P35-LHRH (X-axis concentration of peptides nmoles/well).

Figure 4C:
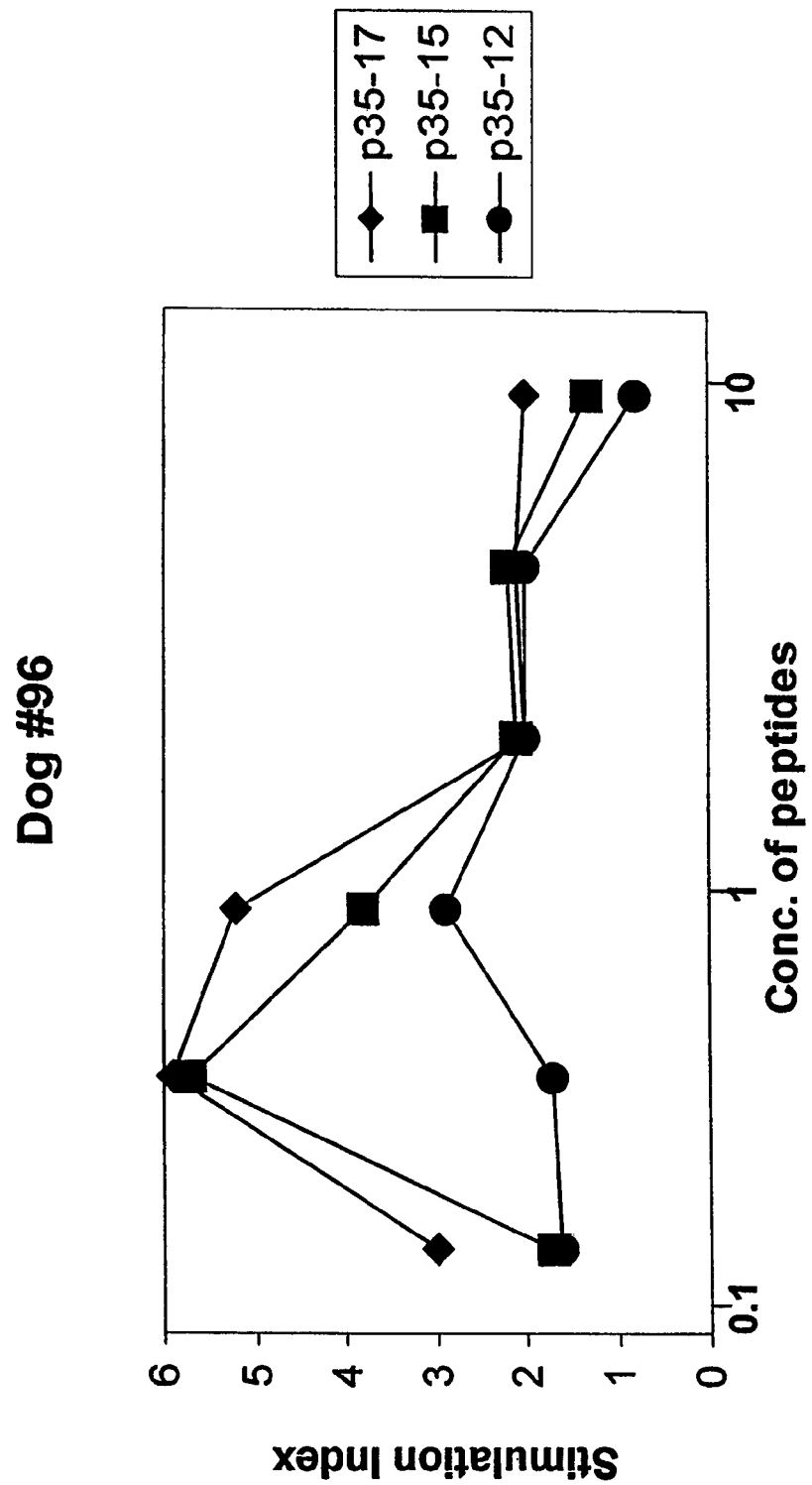

FIG. 4c. Stimulation indices to Th-epitope P35 and its truncated versions in Dog #96 immunised with P35-LHRH (X-axis concentration of peptides nmoles/well).

Figure 4D:
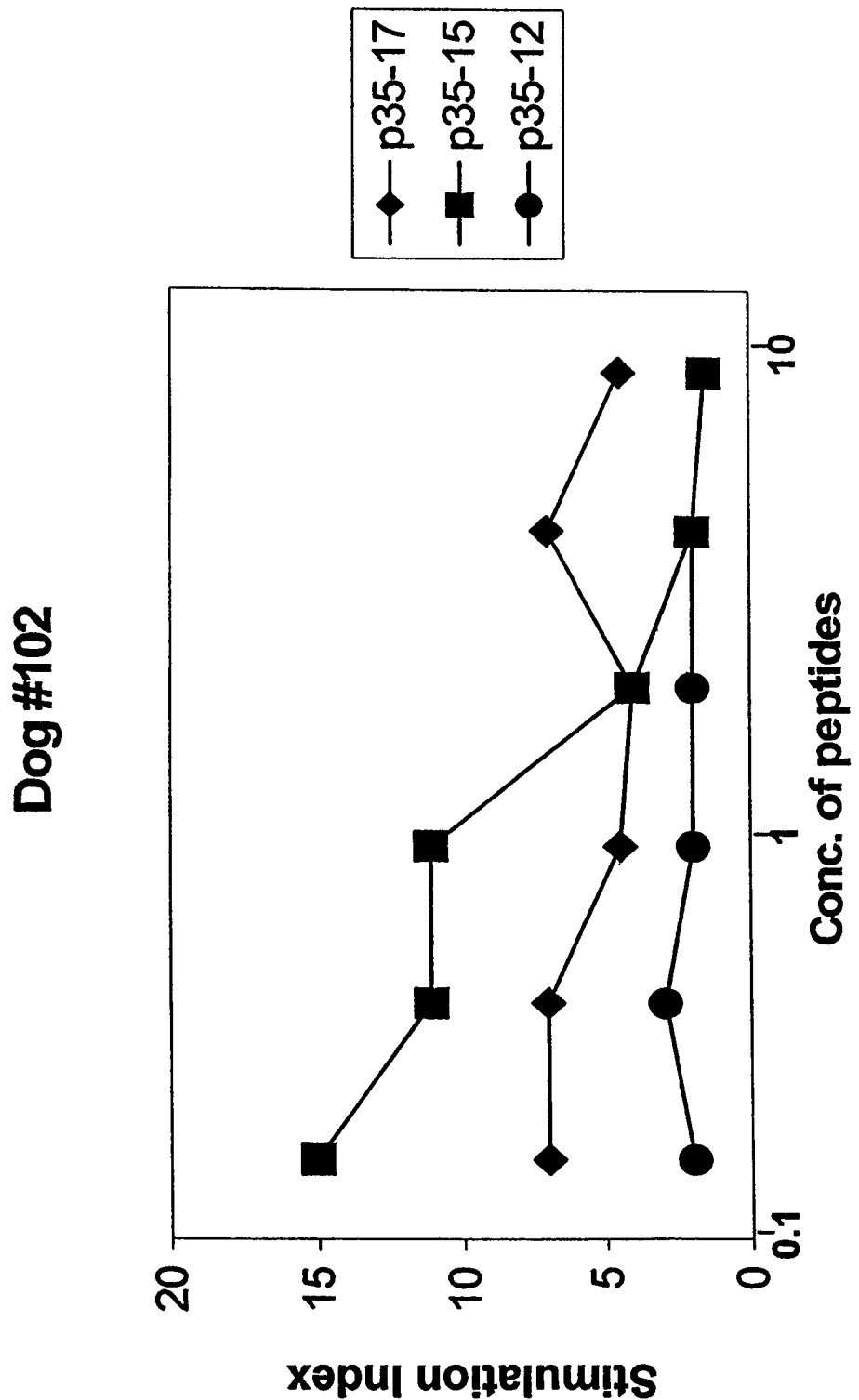

FIG. 4d. Stimulation indices to Th-epitope P35 and its truncated versions in Dog #102 immunised with P35-LHRH (X-axis concentration of peptides nmoles/well).

EXAMPLE 1

Identification of T Helper Cell Epitopes

Methods and Results:

Towards identification of canine T cell epitopes 94, 17 residue overlapping peptides were designed encompassing the entire sequence of fusion protein of canine distemper virus (CDV). The 17mer peptides were numbered sequentially for identification starting from the N-terminus. The sequence of the fusion protein of CDV as determined by Barrett et al 1987 (Virus Res. 8, 373-386) is shown in FIG. 1. The peptides were used in T-cell proliferation assays using peripheral blood lymphocytes (PBMC) from dogs immunised with Canvac™ 3 in 1 vaccine (CSL Limited) which contains live CDV.

Initially, four dogs were used and they were boosted with the Canvac™ 3 in 1 vaccine twice with four to six weeks between each vaccination. The dogs were bled after each booster vaccination and the PBMCs were tested against the peptides. No significant proliferation to peptides was observed.

Since CDV has been reported to be lymphotropic and the vaccine consists of live CDV, there was the possibility that it may be sequestered in lymphoid organs preventing significant numbers of precursor T cells entering the peripheral system. To increase the frequency of peripheral blood anti-CDV T cells dogs were boosted with heat killed CDV (obtained as a pellet from virus culture medium, CSL Limited). Two weeks later, the dogs were bled and the PBMCs tested for proliferation against the peptides. Again there was no proliferation to the peptide antigens.

An alternate strategy was used to increase the precursor frequency of specific T cells recognising the CDV peptides. Fresh PBMCs obtained from these hyperimmunised dogs were subjected to stimulation in vitro with pools of all 94 peptides for 30 minutes at 37° C. The cells were then washed to remove any excess peptides and cultured for 7 days. This population of T cells was then tested with autologous APCs with every single peptide as the antigen. Table 1 shows the peptides to which significant (stimulation index >2) levels of proliferation were observed.

To confirm this observation, the same four dogs were bled again, five weeks after receiving the dose of killed virus. The PBMCs were stimulated in vitro with pools of either all 94 peptides or peptides 21-40 (because most of the activity was in this region) and after 7 days of culture the stimulated T cells were tested against individual peptides. Significant stimulatory indices were obtained with all peptides, confirming the above results. Four more dogs which received only one dose of 3 in 1 vaccine were tested using the in vitro stimulation method and all four dogs responded to the majority of peptides shown in Table 2.

The above peptides were also tested on cells from additional dogs, with results shown in Table 3. Peptides P64, P74 and P75 were also shown to react strongly with peripheral blood mononuclear cells from dogs of various breeds immunised with CDV (Table 4), and are therefore identified as strong T-helper epitopes.

TABLE 1

Identification of canine T cell epitopes from the sequence of fusion protein of CDV.

| Peptides | Beagle Foxhound (Dog #18) | Beagle Foxhound (Dog #19) | Beagle Foxhound (Dog #20) | Beagle Foxhound (Dog #21) |
| --- | --- | --- | --- | --- |
| p2  | 2*  | <2   | 8   | 3.9  |
| p4  | 4.9 | <2   | 3.3 | 4.6  |
| p6  | 2.5 | <2   | 4   | 5.1  |
| p10 | 2.3 | <2   | 3.2 | 9.1  |
| p24 | 5.8 | 9.9  | 2.8 | 29   |
| p25 | 3.2 | 11.9 | 4.5 | 17   |
| p27 | 3.3 | 34   | 6.7 | 14.8 |
| p29 | 3.5 | 42   | 4.4 | <2   |
| p35 | 3.1 | 57   | 3.3 | 22   |
| p36 | 6.7 | 3.7  | 3.3 | 16   |
| p37 | 6.9 | 10.9 | 8.2 | 26   |
| p38 | 2.8 | 6.7  | 3.6 | 4.2  |
| p47 | 3.3 | 85.7 | 2.9 | 1.9  |
| p62 | <2  | 51   | 5.6 | 4.2  |
| p68 | 6.6 | <2   | <2  | 11.7 |

*Stimulatory index

TABLE 2

Identification of canine T cell epitopes from the sequence of fusion protein of CDV.

| Peptides | Beagle Foxhound (Dog #70) | Beagle Foxhound (Dog #71) | Beagle Foxhound (Dog #72) | Beagle Foxhound (Dog #73) |
| --- | --- | --- | --- | --- |
| p8  | 2.2 |     |     |     |
| p22 |     |     | 2.6 |     |
| p24 |     | 3.2 | 2.2 |     |
| p25 | 1.5 | 2.9 | 2   | 12  |
| p27 |     | 2.7 | 3.5 | 4.8 |
| p28 |     | 2   |     |     |
| p29 |     | 2   |     | 6   |
| p33 |     |     | 1.6 |     |
| p35 |     |     | 1.7 | 6.8 |
| p37 |     |     | 1.7 |     |
| p62 |     | 3   |     |     |

TABLE 3

Identification of canine T cell epitopes from the sequence of fusion protein of CDV.

| Peptides | Kelpie Foxhound (Dog #125) | Kelpie Foxhound (Dog #126) |
|---|---|---|
| p23 | 3.2 | |
| p27 | 4.5 | 8.5 |
| p28 | 1.9 | |
| p29 | 3.6 | |
| p33 | 6 | |
| p34 | 2.1 | |
| p35 | 3.8 | 10 |
| p36 | 3 | |
| p37 | 2.5 | |
| p38 | 2.2 | |
| p39 | 2.9 | |
| p47 | 2.7 | |
| p62 | 2.4 | |
| p68 | 2.9 | |

TABLE 4

Identification of canine T cell epitopes from the sequence of fusion protein of CDV.

| Peptides | Poodle Shitzu | Beagle Foxhound #18 | Beagle Foxhound #19 | Beagle Foxhound #20 | Beagle Foxhound #21 |
|---|---|---|---|---|---|
| P64 | 50.0 | | 2.5 | 2.5 | |
| P74 | 4.0 | | | 1.7 | 6.0 |
| P75 | 10 | 2.5 | | | 7.2 |

Once again the same peptides and one additional peptide P32 were tested on cells from additional dogs. These peptides were also shown to react strongly with peripheral blood mononuclear cells from dogs of various breeds immunised with CDV (Table 5), and are therefore identified as strong T-helper epitopes.

In conclusion, 26 peptides were identified as canine T helper cell epitopes in the fusion protein of CDV. The sequences of each of these peptides are set out in Table 6.

These T helper cell epitopes will have usefulness as components of animal, in particular, canine vaccines, either simply as synthetic peptide based vaccines and as additions to vaccines containing more complex antigens.

TABLE 5

Identification of canine T cell epitopes from the sequence of fusion protein of CDV.

| Peptides | Poodle Shitzu | Grey hound | Fox Terrier | Terrier Cross | Kelpie Pointer | Border Collie |
|---|---|---|---|---|---|---|
| P2  | 140 | <2 | <2 | <2 | 2.6 | 2 |
| P4  | 44  | 2  | <2 | 2  | 3.5 | 2 |
| P6  | 38  | <2 | <2 | <2 | <2  | 2 |
| P8  | 100 | 2  | <2 | <2 | 2.8 | 2 |
| P10 | 50  | 2  | 2.2 | 2.1 | 2.4 | 3 |
| P25 | <2  | <2 | 2.6 | <2 | 2.6 | <2 |
| P29 | 2   | <2 | <2 | 2  | <2  | <2 |
| P32 | <2  | 2  | <2 | <2 | <2  | <2 |
| P33 | <2  | <2 | <2 | <2 | 2   | 2 |
| P35 | <2  | <2 | 2.2 | <2 | 2   | 2 |
| P37 | <2  | <2 | <2 | 2  | 2   | <2 |
| P62 | 24  | <2 | <2 | <2 | <2  | <2 |
| P64 | 50  | <2 | <2 | <2 | <2  | <2 |
| P68 | 5   | <2 | <2 | <2 | <2  | <2 |
| P74 | 4   | <2 | <2 | <2 | <2  | <2 |
| P75 | 10  | <2 | <2 | <2 | <2  | <2 |

TABLE 6

Sequences of the peptides:

| | |
|---|---|
| P2  | SSKTQTHTQQDRPPQPS (SEQ ID NO: 1) |
| P4  | QPSTELEETRTSRARHS (SEQ ID NO: 2) |
| P6  | RHSTTSAQRSTHYDPRT (SEQ ID NO: 3) |
| P8  | PRTSDRPVSYTMNRTRS (SEQ ID NO: 4) |
| P10 | TRSRKQTSHRLKNIPVH (SEQ ID NO: 5) |
| P24 | SHQYLVIKLIPNASLIE (SEQ ID NO: 6) |
| P22 | IGTDNVHYKIMTRPSHQ (SEQ ID NO: 7) |
| P23 | YKIMTRPSHQYLVIKLI (SEQ ID NO: 8) |
| P25 | KLIPNASLIENCTKAEL (SEQ ID NO: 9) |
| P27 | AELGEYEKLLNSVLEPI (SEQ ID NO: 10) |
| P28 | KLLNSVLEPINQALTLM (SEQ ID NO: 11) |
| P29 | EPINQALTLMTKNVKPL (SEQ ID NO: 12) |
| P32 | SGRRQRRFAGVVLAGVA (SEQ ID NO: 26) |
| P33 | FAGVVLAGVALGVATAA (SEQ ID NO: 13) |
| P34 | GVALGVATAAQITAGIA (SEQ ID NO: 14) |
| P35 | TAAQITAGIALHQSNLN (SEQ ID NO: 15) |
| P36 | GIALHQSNLNAQAIQSL (SEQ ID NO: 16) |
| P37 | NLNAQAIQSLRTSLEQS (SEQ ID NO: 17) |

TABLE 6-continued

Sequences of
the peptides:

| | |
|---|---|
| P38 | QSLRTSLEQSNKAIEEI (SEQ ID NO: 18) |
| P39 | EQSNKAIEEIREATQET (SEQ ID NO: 19) |
| P47 | TELLSIFGPSLRDPISA (SEQ ID NO: 20) |
| P62 | PRYIATNGYLISNFDES (SEQ ID NO: 21) |
| P68 | CIRGDTSSCARTLVSGT (SEQ ID NO: 22) |
| P64 | DESSCVFVSESAICSQN (SEQ ID NO: 23) |
| P74 | TSTIINQSPDKLLTFIA (SEQ ID NO: 24) |
| P75 | SPDKLLTFIASDTCPLV (SEQ ID NO: 25) |

Selected sequences of the identified T-cell epitopes were tested for their ability to induce an antibody response to a linked B-cell epitope. Trials were conducted in dogs for assessment of antibody responses. The T-cell epitopes were linked to the B cell epitope LHRH (leuteinising hormone releasing hormone), with the T-cell epitope at the N-terminus and LHRH positioned at the carboxy terminus.

Peptides were synthesised using standard chemistry with Fmoc protection. All peptides were purified to at least 80% purity and the product checked by mass spectroscopy.

The peptides were produced as contiguous T-cell—B cell determinants. The LHRH sequence of Pyro Glu-His-Trp-Ser-Tyr-Gly-Leu-Arg-Pro-Gly (SEQ ID NO: 28), or variations of it, was linked to the carboxyl terminus of each respective CDV T- helper epitope.

In-vivo evaluation of some of the T-helper epitopes was conducted in two trials, by vaccination of dogs with T-helper—LHRH sequences.

EXAMPLE 2

Trial K9-5

A total of 14 dogs of mixed sex were used in this trial. All had been previously vaccinated with a live CDV vaccine and had also been vaccinated against LHRH.

Vaccine Formulation.

Test peptides P25, P27, P35 from CDV were synthesised with LHRH at the C terminus of each T-helper epitope. The LHRH sequence used was the full 10 amino acids of the native LHRH. Each of the vaccine constructs, together with a control peptide comprising a mouse influenza T-cell epitope linked to a repeat malarial B-cell epitope (sequence shown in table below) were purified to 80-90% purity. All peptides were dissolved in 4M urea before dilution with sterile saline to an appropriate volume to give 40nmoles per 1 mL dose. Iscomatrix™ was added to a final concentration of 150 ug/1 mL dose as adjuvant together with thiomersal preservative (0.01%).

ISCOM™ or Immunostimulating Complex (Barr, Sjolander and Cox, 1998, Advanced Drug Delivery Systems 32: 247-271) are a well characterised class of adjuvant comprised of a complex of phospholipid, cholesterol and saponin, usually with a protein incorporated into the complex. Where the complex is formed in the absence of protein antigen, then this complex is termed Iscomatrix™. The saponin used in the preparation of this adjuvant was Quil A.

Vaccination, Blood Samples and Assays.

All dogs were vaccinated with a 1 mL dose, delivered in the scruff of the neck. Vaccinations were given at 0 and 4 weeks and venous blood samples were obtained at intervals during the trial.

Effective T-cell help was determined by measuring the antibody response to LHRH by ELISA. Biological effectiveness of the peptide based vaccine was determined by measuring the levels of progesterone in female dogs and testosterone in male dogs.

TABLE 7

Trial Groups

| Peptide | Dog Nos. |
|---|---|
| Control-ALNNRFQIKGVELKS-(NANP)3 (SEQ ID NO: 30) | 104, 998 |
| P25-LHRH 1-10 | 70, 73, 127, 993 |
| P27-LHRH 1-10 | 20, 94, 101, 105 |
| P35-LHRH 1-10 | 19, 96, 100, 102 |

Results

Pre-existing low antibody levels to LHRH were present in all dogs due to immunisation previously with a different vaccine. The control group of dogs exhibited a slow decrease in antibody levels.

Dogs immunised with P25-LHRH, P27-LHRH and P35-LHRH all showed strong antibody responses to the B-cell epitope (LHRH). This response persisted to 6 weeks post boost vaccination (see Table 8).

The biological potency of the vaccine was demonstrated by a significant reduction in progesterone or testosterone levels (see Tables 9 and 10).

TABLE 8

Anti LHRH Titres

| Peptide | Dog No | Prebleeds | 2 wks post boost | 6 wks post boost |
|---|---|---|---|---|
| Control | 104 | 1258 | 1975 | 1936 |
| | 998 | 2559 | 1982 | 1947 |
| Average | | 1794 | 1978 | 1941 |
| Range | | 1258-2559 | 1975-1982 | 1936-1947 |
| P25-LHRH | 70 | 856 | 24245 | 16697 |
| (1-10) | 73 | | 42665 | 16922 |
| | 127 | 1361 | 21485 | 19662 |
| | 993 | 577 | 24879 | 15119 |
| Average | | 886 | 23120 | 17242 |
| Range | | 0-1361 | 21485-42665 | 15119-19662 |
| p27-LHRH | 20 | 747 | 29653 | 8423 |
| (1-10) | 94 | | 41247 | 22759 |
| | 101 | 4256 | 52724 | 17353 |
| | 105 | 944 | 12600 | 8366 |
| Average | | 2004 | 25774 | 12049 |
| Range | | 747-4256 | 12600-52724 | 8366-22759 |
| p35-LHRH | 19 | 665 | 18033 | 6228 |
| (1-10) | 96 | 1621 | 26583 | 5744 |
| | 100 | 580 | 17255 | 4829 |
| | 102 | 180 | 11740 | 2963 |
| Average | | 323 | 14233 | 3783 |
| Range | | 180-1621 | 11740-26583 | 2963-6228 |

TABLE 9

Progesterone results (nmol/L)

| Peptide | Dog No. | 4 wks post primary | 2 wks post boost | 6 wks post boost |
|---|---|---|---|---|
| Control | 998 | 5.17 | 4.28 | <0 |
| p25-LHRH (1-10) | 127 | 3.04 | 4.83 | <0 |
|  | 993 | 1.7 | 0.87 | <0 |
| p27-LHRH (1-10) | 101 | 0.42 | 0.14 | <0 |
| p35-LHRH (1-10) | 96 | 31.76 | 2.15 | <0 |
|  | 100 | <0 | <0 | <0 |

TABLE 10

Testosterone results (nmol/L)

| Peptide | Dog No. | 4 wks post primary | 2 wks post boost | 6 wks post boost |
|---|---|---|---|---|
| Control | 104 | 9.69 | 2.51 | 3.31 |
| p25-LHRH (1-10) | 70 | <0 | <0 | <0 |
|  | 73 | 5.38 | <0 | <0 |
| p27-LHRH (1-10) | 20 | 1.04 | <0 | <0 |
|  | 94 | 3.33 | <0 | <0 |
|  | 105 | >47.7 | <0 | <0 |
| p35-LHRH (1-10) | 19 | 4.3 | 2.77 | 4.55 |
|  | 102 | 6.72 | <0 | <0 |

The effectiveness of selected T-cell epitopes from the F-protein of CDV in providing T-cell help to elicit antibody responses in dogs proves that the identified sequences are functional. These results also validate the scientific approach and usefulness of the in vitro screening method for identifying T-helper epitope sequences with in vivo activity.

EXAMPLE 3

Trial K9-8

A total of 35 dogs mixed sex were used in this trial. All had been previously vaccinated with a live CDV vaccine but had not been vaccinated against LHRH.

Vaccine Formulation:

The T-Helper epitopes were linked to a truncated form of LHRH, containing amino acids 2 to 10 of the native 10 amino acid sequence, as shown below:

```
2-10    His-Trp-Ser-Tyr-Gly-Leu-Arg-    (SEQ ID NO: 29)
LHRH    Pro-Gly.
```

All vaccines were formulated as for Example 2, ie each 1 mL dose of vaccine contained 40nmoles of peptide, 150 μg Iscomatrix™, and thiomersal as preservative.

Where dogs were vaccinated with a pool of peptides, the concentration of each peptide was adjusted to give equal concentrations and a total amount of 40 nmoles of LHRH epitope per 1 mL dose.

Vaccination, Blood Samples and Assays.

All dogs were vaccinated with a 1 mL dose, delivered in the scruff of the neck. Vaccinations were given at 0 and 4 weeks and venous blood samples were obtained at intervals during the trial.

Effective T-cell help was determined by measuring the antibody response to LHRH by ELISA. Biological effectiveness of the peptide based vaccine was determined by measuring the levels of progesterone in female dogs and testosterone in male dogs.

TABLE 11

Trial Groups

| Peptide Group | Dog Nos. |
|---|---|
| P25-LHRH 2-10 | 211, 195, 197, 181 |
| P27-LHRH 2-10 | 203, 191, 186, 201 |
| P35-LHRH 2-10 | 217, 198, 187, 196 |
| Pool: P25-LHRH 2-10, P27-LHRH 2-10, P35-LHRH 2-10 | 212, 193, 178, 216, Y3 |
| P2-LHRH 2-10 | 194, 199, 179, 220 |
| P8-LHRH 2-10 | Y4, Y6, 160, 200 |
| P62-LHRH 2-10 | 219, 185, 221, 177 |
| P75-LHRH 2-10 | 189, 222, 202, 176 |
| Unvaccinated controls | 190, 159 |

Results

Strong antibody responses to LHRH were demonstrated in dogs immunised with the T-cell-LHRH constructs with the T-cell epitopes P25, P27, P35, P62, P75, and the pool of T-cell-LHRH peptides comprising a combination of T-cell epitopes P25, P27 and P35 (see Table 12).

Low to undetectable antibody responses were seen in dogs immunised with P2 and P8-LHRH peptides (see Table 12). This was concluded to indicate that these T-cell peptides were not well recognised by Beagle-Foxhound dogs, which is consistent with their identification using PBMCs' from other dog breeds. The initial screening in Beagle foxhound dogs indicated that this breed of dog does not respond to these 2 T-cell epitopes.

As is well understood by those skilled in the art of peptide vaccines the response to individual peptides is genetically determined. The class II Major Histocompatability Complex (MHC II) is polymorphic. Class II molecules at the cell surface function to bind peptides for presentation to T-cells, which is required as part of the activation process for T-cells, including helper T-cells. The allelic forms of MHC class II bind discrete sets of peptide antigens, and thus the response to those antigens is genetically determined. Thus the results are interpreted to indicate that the Beagle—Foxhound breed of dog does not possess the appropriate MHC-II alleles to respond to P2 and P8, but that other breeds of dog do, eg. the Poodle Shitzu breed that were used to identify these peptides.

Control dogs showed no change in antibody levels to LHRH during the trial period and hormone levels were within normal ranges for the age and sex of the dogs (see Table 12).

TABLE 12

Anti-LHRH Titres

| Peptide | Group | Dog No | 4 wks after primary | 2 wks post boost | 4 wks post boost |
|---|---|---|---|---|---|
| Control | 1 | 159 | 0 | 0 | 0 |
|  | 1 | 190 | 0 | 0 | 0 |
|  | GMT |  |  |  |  |
| Pool | 2 | Y3 | 1860 | 55659 | 95038 |
|  | 2 | 178 | 17900 | 416036 | 486793 |
|  | 2 | 193 | 8770 | 211369 | 189143 |
|  | 2 | 212 | 3766 | 121411 | 135293 |
|  | 2 | 216 | 8378 | 294769 | 642293 |
|  | GMT |  | 6207 | 177292 | 237798 |
| P25-LHRH | 3 | 181 | 1893 | 152264 | 131643 |
|  | 3 | 195 | 31197 | 205906 | 455193 |
|  | 3 | 197 | 14423 | 337698 | 240543 |
|  | 3 | 211 | 20607 | 142798 | 131643 |
|  | GMT |  | 11510 | 193037 | 214229 |

TABLE 12-continued

Anti-LHRH Titres

| Peptide | Group | Dog No | 4 wks after primary | 2 wks post boost | 4 wks post boost |
|---|---|---|---|---|---|
| P27-LHRH | 4 | 186 | 0 | 11206 | 17263 |
| | 4 | 191 | 0 | 59154 | 125493 |
| | 4 | 201 | 0 | 17041 | 34103 |
| | 4 | 203 | 0 | 1000 | 857 |
| | GMT | | 0 | 18523 | 26698 |
| P35-LHRH | 5 | 187 | 2009 | 141775 | 55797 |
| | 5 | 196 | 4868 | 237208 | 158040 |
| | 5 | 198 | 1539 | 154375 | 68307 |
| | 5 | 217 | 0 | 121050 | 40822 |
| | GMT | | 2469 | 103085 | 58002 |
| P2-LHRH | 6 | 179 | 0 | 0 | 0 |
| | 6 | 194 | 0 | 0 | 0 |
| | 6 | 199 | 0 | 0 | 0 |
| | 6 | 220 | 0 | 0 | 0 |
| | GMT | | | | |
| P8-LHRH | 7 | Y4 | 0 | 0 | 0 |
| | 7 | Y6 | 0 | 0 | 0 |
| | 7 | 160 | 0 | 1200 | ND |
| | 7 | 200 | 0 | 8000 | 2227 |
| | GMT | | | | |
| P62-LHRH | 8 | 177 | 1242 | 3821 | 2985 |
| | 8 | 185 | 0 | 146581 | 67461 |
| | 8 | 219 | 0 | 29353 | 28282 |
| | 8 | 221 | 2697 | 231473 | 156549 |
| | GMT | | 1830 | 44167 | 30728 |
| P75-LHRH | 9 | 176 | 0 | 12177 | 5559 |
| | 9 | 189 | 0 | 15795 | 17155 |
| | 9 | 202 | 0 | 2121 | 2216 |
| | 9 | 222 | 0 | 9787 | 7879 |
| | GMT | | | 11201 | 8746 |

EXAMPLE 4

In Vitro T Cell Proliferation Assays to demonstrate recognition of Th-epitope Incorporated in the Peptide Vaccines To demonstrate recognition of the Th-epitope within the peptide immunogen PBMCs obtained from dogs immunised with peptide vaccines (dogs from Example 2) were tested against the respective Th-epitopes. The assay was carried out without the enrichment of PBMCs. PBMCs obtained from Ficoll gradient purification were directly tested against the respective Th-epitope and its truncated versions. The study demonstrated that all the dogs immunised with peptide vaccines responded to the Th-epitope incorporated confirming that T-cell activity resides in the respective sequences (FIGS. 2-4). Truncated versions of the respective Th-epitopes were also tested to more closely define the T-cell activity within the sequences. It was observed that for P25 the full sequence of 17 residues was better than the shorter peptides of 15 and 12 residues, each truncated from the N-terminus of the sequence (FIG. 2). This implies that the T-cell activity is towards the N-terminus or middle of the 17-residue peptide.

A similar observation was made with P27, the 17 residue long peptide was a better simulator than the 15-mer truncated from the N-terminus (FIG. 3). This observation again suggested that the T-cell activity may reside towards the middle or the N-terminus of the full length peptide.

In the case of P35 and its shorter versions, except for one dog (#102), the other three dogs responded as well to the 12 residue peptide as to the full length 17 residue one (FIG. 4). In dog #102 the 15 residue peptide was more stimulatory than the full length peptide. From this it can be deduced that that the first two residues in the sequence of P35 may not be essential and that the activity is towards the middle or C-terminus of the peptide.

EXAMPLE 5

Trial in BALB/c Mice

The canine vaccines with CDV-F derived Th-epitopes and LHRH used in Example 3 were also used to immunise BALB/c mice to investigate if the Th-epitopes would be functional in a different animal species.

Vaccine Formulation

All vaccines were formulated as for Example 3 except that they were diluted further so that 100 μl doses contained 2.7 nmoles of peptide and 10 μg of Iscomatrix™ and thiomersol as preservative.

Vaccination, Blood Samples and Assays.

Mice were vaccinated with 100 μl of the vaccine at the base of tail. Vaccinations were given at 0 and 4 weeks and animals bled at intervals after each vaccination from the retro-orbital plexus. Effective T-cell help was determined by measuring the antibody response to LHRH by ELISA.

Results

Mice immunised with P25-LHRH and pool of peptides comprising of P25-LHRH, P27-LHRH and P35-LHRH generated high antibody titres to LHRH. Peptides P35 and P75 generated low antibody titres whereas mice immunised P2, P8 and P62 had undetectable levels of anti-LHRH antibodies (Table 13).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 13

Anti-LHRH antibody titres in mice immunised with CDV-F derived T cell epitope-LHRH vaccines

| Groups | 4 weeks post first vaccination | | | | | 2 weeks post second vaccination | | | | |
|---|---|---|---|---|---|---|---|---|---|---|
| | Mouse 1 | Mouse 2 | Mouse 3 | Mouse 4 | Mouse 5 | Mouse 1 | Mouse 2 | Mouse 3 | Mouse 4 | Mouse 5 |
| Group 1 (control) | <100 | <100 | | | | <100 | <100 | | | |
| Group 2 (pool) | 100 | 126 | 200 | 126 | 200 | 16,000 | 16,000 | 16,000 | 16,000 | 16,000 |
| Group 3 (p25-LHRH) | 126 | 400 | 282 | 100 | 282 | 16,000 | 16,000 | 16,000 | 16,000 | 16,000 |

TABLE 13-continued

Anti-LHRH antibody titres in mice immunised with CDV-F derived T cell epitope-LHRH vaccines

| Groups | 4 weeks post first vaccination | | | | | 2 weeks post second vaccination | | | | |
|---|---|---|---|---|---|---|---|---|---|---|
| | Mouse 1 | Mouse 2 | Mouse 3 | Mouse 4 | Mouse 5 | Mouse 1 | Mouse 2 | Mouse 3 | Mouse 4 | Mouse 5 |
| Group 5 (p35-LHRH) | <100 | <100 | <100 | <100 | <100 | 1,412 | 800 | <100 | <100 | <100 |
| Group 6 (p2-LHRH) | <100 | <100 | | | | <100 | <100 | | | |
| Group 7 (p8-LHRH | <100 | <100 | <100 | <100 | | <100 | <100 | <100 | <100 | |
| Group 8 (p62-LHRH | <100 | <100 | <100 | | | 126 | 126 | <100 | | |
| Group 9 (p75-LHRH | <100 | <100 | <100 | <100 | <100 | <100 | <100 | 316 | 3,162 | <100 |

We claim:

1. A T helper cell epitope, the epitope being contained within a peptide sequence selected from the group consisting of RHSTTSAQRSTHYDPRT (SEQ ID NO: 3); GIALHQSNLNAQAIQSL (SEQ ID NO: 16): CIRGDTSSCARTLVSGT (SEQ ID NO: 22); and TSTIINQSPDKLLTFIA (SEQ ID NO: 24).

2. A composition for use in raising an immune response in an animal, the composition comprising at least one T helper cell epitope, the at least one T helper cell epitope being contained within a peptide sequence selected from the group consisting of RHSTTSAQRSTHYDPRT (SEQ ID NO: 3); GIALHQSNLNAQAIQSL (SEQ ID NO: 16): CIRGDTSSCARTLVSGT (SEQ ID NO: 22); and TSTIINQSPDKLLTFIA (SEQ ID NO: 24).

3. A composition as claimed in claim 2 in which the composition comprises at least one peptide selected from the group consisting of RHSTTSAQRSTHYDPRT (SEQ ID NO: 3); GIALHQSNLNAQAIQSL (SEQ ID NO: 16); CIRGDTSSCARTLVSGT (SEQ ID NO; 22); and TSTIINQSPDKLLTFIA (SEQ ID NO: 24).

4. A composition as claimed in claim 2 in which the composition further comprises at least one B cell epitope and/or at least one CTL epitope.

5. A composition as claimed in claim 4 in which the at least one B cell epitope and/or the at least one CTL epitope are linked to at least one of the T helper cell epitopes.

6. A composition as claimed in claim 5 in which the composition comprises a plurality of epitope constructs in which each conjugate comprises at least one T helper cell epitope and at least one B cell epitope.

7. A composition as claimed in claim 5 in which the composition comprises a plurality of epitope constructs in which each conjugate comprises at least one T helper cell epitope and at least one CTL epitope.

8. A composition as claimed in claim 4 in which the composition comprises an LHRH B cell epitope.

9. A composition as claimed in claim 2 in which the composition comprises a plurality of T helper cell epitopes.

10. A composition as claimed in claim 9 in which the plurality of T cell epitopes is a single polypeptide.

11. A composition as claimed in claim 9 in which the composition further comprises at least one B cell epitope and/or at least one CTL epitope.

12. A composition as claimed in claim 11 in which the least one B cell epitope and/or at least one CTL epitope is linked to the plurality of T helper cell epitopes.

13. A composition as claimed in claim 11 in which the composition comprises an LHRH B cell epitope.

14. A composition as claimed in claim 2 in which the composition comprises an adjuvant.

15. A composition as claimed in claim 14 in which the adjuvant comprises ISCOMs or Iscomatrix.

16. A method of inducing an immune response in an animal, the method comprising administering to the animal the composition as claimed in claim 2.

* * * * *